United States Patent
Smith et al.

(10) Patent No.: US 12,311,198 B2
(45) Date of Patent: *May 27, 2025

(54) FLASH THERAPY TREATMENT PLANNING AND ONCOLOGY INFORMATION SYSTEM HAVING DOSE RATE PRESCRIPTION AND DOSE RATE MAPPING

(71) Applicants: Siemens Healthineers International AG, Steinhausen (CH); Varian Medical Systems Particle Therapy GmBH & Co. KG, Troisdorf (DE)

(72) Inventors: Christel Smith, Santa Barbara, CA (US); Timo Koponen, Espoo (FI); Reynald Vanderstraeten, Uccle (BE); Anthony Magliari, Newark, IL (US); Eric Abel, San Jose, CA (US); Jessica Perez, Geneva (CH); Michael Folkerts, Costa Mesa, CA (US); Deepak Khuntia, Los Altos, CA (US)

(73) Assignees: SIEMENS HEALTHINEERS INTERNATIONAL AG, Steinhausen (CH); VARIAN MEDICAL SYSTEMS PARTICLE THERAPY GMBH & CO. KG, Troisdorf (DE)

( * ) Notice: Subject to any disclaimer, the term of this patent is extended or adjusted under 35 U.S.C. 154(b) by 0 days.

This patent is subject to a terminal disclaimer.

(21) Appl. No.: 18/499,745

(22) Filed: Nov. 1, 2023

(65) Prior Publication Data

US 2024/0075314 A1    Mar. 7, 2024

Related U.S. Application Data

(63) Continuation of application No. 18/087,398, filed on Dec. 22, 2022, now Pat. No. 11,865,364, which is a
(Continued)

(51) Int. Cl.
| | | |
|---|---|---|
| A61N 5/10 | (2006.01) | |
| G16H 20/40 | (2018.01) | |
| G16H 10/60 | (2018.01) | |

(52) U.S. Cl.
CPC ......... *A61N 5/1031* (2013.01); *A61N 5/1045* (2013.01); *A61N 5/1071* (2013.01);
(Continued)

(58) Field of Classification Search
None
See application file for complete search history.

(56) References Cited

U.S. PATENT DOCUMENTS

| | | |
|---|---|---|
| 1,009,806 A | 11/1911 | Thompson |
| 4,163,901 A | 8/1979 | Azam et al. |

(Continued)

FOREIGN PATENT DOCUMENTS

| | | |
|---|---|---|
| CN | 104001270 A | 8/2014 |
| CN | 106730407 A | 5/2017 |

(Continued)

OTHER PUBLICATIONS

M. McManus et al., "The challenge of ionisation chamber dosimetry in ultra-short pulsed high dose-rate Very High Energy Electron beams," Sci Rep 10, 9089 (2020), published Jun. 3, 2020,; rattps://doi.org/10.1038/s41598-020-65819-y.
(Continued)

*Primary Examiner* — Hoon K Song
(74) *Attorney, Agent, or Firm* — Harness, Dickey & Pierce, P.L.C.

(57) ABSTRACT

A computing system comprising a central processing unit (CPU), and memory coupled to the CPU and having stored therein instructions that, when executed by the computing system, cause the computing system to execute operations to generate a radiation treatment plan. The operations include
(Continued)

accessing a minimum prescribed dose to be delivered into and across the target, determining a number of beams and directions of the beams, and determining a beam energy for each of the beams, wherein the number of beams, the directions of the beams, and the beam energy for each of the beams are determined such that the entire target receives the minimum prescribed dose. The operations further include prescribing a dose rate and optimizing dose rate constraints for FLASH therapy, and displaying a dose rate map of the FLASH therapy.

17 Claims, 9 Drawing Sheets

Related U.S. Application Data continuation of application No. 17/147,353, filed on Jan. 12, 2021, now Pat. No. 11,554,271, which is a continuation of application No. 16/436,762, filed on Jun. 10, 2019, now Pat. No. 10,918,886.

(52) U.S. Cl.
CPC ........... *G16H 20/40* (2018.01); *A61N 5/1043* (2013.01); *G16H 10/60* (2018.01)

(56) References Cited

U.S. PATENT DOCUMENTS

| | | | |
|---|---|---|---|
| 4,914,681 | A | 4/1990 | Klingenbeck et al. |
| 5,153,900 | A | 10/1992 | Nomikos et al. |
| 5,267,294 | A | 11/1993 | Kuroda et al. |
| 5,341,292 | A | 8/1994 | Zamenhof |
| 5,550,378 | A | 8/1996 | Skillicorn et al. |
| 5,610,967 | A | 3/1997 | Moorman et al. |
| 5,625,663 | A | 4/1997 | Swerdloff et al. |
| 5,682,412 | A | 10/1997 | Skillicorn et al. |
| 5,757,885 | A | 5/1998 | Yao et al. |
| 6,198,802 | B1 | 3/2001 | Elliott et al. |
| 6,222,544 | B1 | 4/2001 | Tarr et al. |
| 6,234,671 | B1 | 5/2001 | Solomon et al. |
| 6,260,005 | B1 | 7/2001 | Yang et al. |
| 6,379,380 | B1 | 4/2002 | Satz |
| 6,411,675 | B1 | 6/2002 | Llacer |
| 6,445,766 | B1 | 9/2002 | Whitham |
| 6,504,899 | B2 | 1/2003 | Pugachev et al. |
| 6,580,940 | B2 | 6/2003 | Gutman |
| 6,993,112 | B2 | 1/2006 | Hesse |
| 7,268,358 | B2 | 9/2007 | Ma et al. |
| 7,453,983 | B2 | 11/2008 | Schildkraut et al. |
| 7,515,681 | B2 | 4/2009 | Ebstein |
| 7,522,706 | B2 | 4/2009 | Lu et al. |
| 7,560,715 | B2 | 7/2009 | Pedroni |
| 7,590,219 | B2 | 9/2009 | Maurer, Jr. et al. |
| 7,616,735 | B2 | 11/2009 | Maciunas et al. |
| 7,622,623 | B2 | 11/2009 | Fridman et al. |
| 7,623,623 | B2 | 11/2009 | Raanes et al. |
| 7,778,691 | B2 | 8/2010 | Zhang et al. |
| 7,807,982 | B2 | 10/2010 | Nishiuchi et al. |
| 7,831,289 | B2 | 11/2010 | Riker et al. |
| 7,835,492 | B1 | 11/2010 | Sahadevan |
| 7,907,699 | B2 | 3/2011 | Long et al. |
| 8,284,898 | B2 | 10/2012 | Ho et al. |
| 8,306,184 | B2 | 11/2012 | Chang et al. |
| 8,401,148 | B2 | 3/2013 | Lu et al. |
| 8,406,844 | B2 | 3/2013 | Ruchala et al. |
| 8,559,596 | B2 | 10/2013 | Thomson et al. |
| 8,600,003 | B2 | 12/2013 | Zhou et al. |
| 8,613,694 | B2 | 12/2013 | Walsh |
| 8,636,636 | B2 | 1/2014 | Shukla et al. |
| 8,644,571 | B1 | 2/2014 | Schulte et al. |
| 8,716,663 | B2 | 5/2014 | Brusasco et al. |
| 8,836,332 | B2 | 9/2014 | Shvartsman et al. |
| 8,847,179 | B2 | 9/2014 | Fujitaka et al. |
| 8,903,471 | B2 | 12/2014 | Heid |
| 8,917,813 | B2 | 12/2014 | Maurer, Jr. |
| 8,948,341 | B2 | 2/2015 | Beckman |
| 8,958,864 | B2 | 2/2015 | Amies et al. |
| 8,983,573 | B2 | 3/2015 | Carlone et al. |
| 8,986,186 | B2 | 3/2015 | Zhang et al. |
| 8,992,404 | B2 | 3/2015 | Graf et al. |
| 8,995,608 | B2 | 3/2015 | Zhou et al. |
| 9,018,603 | B2 | 4/2015 | Loo et al. |
| 9,033,859 | B2 | 5/2015 | Fieres et al. |
| 9,079,027 | B2 | 7/2015 | Agano et al. |
| 9,149,656 | B2* | 10/2015 | Tanabe ................ A61N 5/1083 |
| 9,155,908 | B2 | 10/2015 | Meltsner et al. |
| 9,233,260 | B2 | 1/2016 | Slatkin et al. |
| 9,258,876 | B2 | 2/2016 | Cheung et al. |
| 9,283,406 | B2 | 3/2016 | Prieels |
| 9,308,391 | B2 | 4/2016 | Liu et al. |
| 9,330,879 | B2 | 5/2016 | Lewellen et al. |
| 9,333,374 | B2 | 5/2016 | Iwata |
| 9,468,777 | B2 | 10/2016 | Fallone et al. |
| 9,469,298 | B2 | 10/2016 | Hayasaka |
| 9,517,358 | B2 | 12/2016 | Velthuis et al. |
| 9,526,918 | B2 | 12/2016 | Kruip |
| 9,545,444 | B2 | 1/2017 | Strober et al. |
| 9,583,302 | B2 | 2/2017 | Figueroa Saavedra et al. |
| 9,636,381 | B2 | 5/2017 | Basile |
| 9,636,525 | B1 | 5/2017 | Sahadevan |
| 9,649,298 | B2 | 5/2017 | Djonov et al. |
| 9,656,098 | B2 | 5/2017 | Goer |
| 9,694,204 | B2 | 7/2017 | Hårdemark |
| 9,776,017 | B2 | 10/2017 | Flynn et al. |
| 9,786,054 | B2 | 10/2017 | Taguchi et al. |
| 9,786,093 | B2 | 10/2017 | Svensson |
| 9,786,465 | B2 | 10/2017 | Li et al. |
| 9,795,806 | B2 | 10/2017 | Matsuzaki et al. |
| 9,801,594 | B2 | 10/2017 | Boyd et al. |
| 9,844,358 | B2 | 12/2017 | Wiggers et al. |
| 9,854,662 | B2 | 12/2017 | Mishin |
| 9,884,206 | B2 | 2/2018 | Schulte et al. |
| 9,931,522 | B2 | 4/2018 | Bharadwaj et al. |
| 9,962,562 | B2 | 5/2018 | Fahrig et al. |
| 9,974,977 | B2 | 5/2018 | Lachaine et al. |
| 9,987,502 | B1 | 6/2018 | Gattiker et al. |
| 10,007,961 | B2 | 6/2018 | Grudzinski et al. |
| 10,022,564 | B2 | 7/2018 | Thieme et al. |
| 10,071,264 | B2 | 9/2018 | Liger |
| 10,080,912 | B2 | 9/2018 | Kwak et al. |
| 10,092,774 | B1 | 10/2018 | Vanderstraten et al. |
| 10,183,179 | B1 | 1/2019 | Smith et al. |
| 10,188,875 | B2 | 1/2019 | Kwak et al. |
| 10,206,871 | B2 | 2/2019 | Lin et al. |
| 10,212,800 | B2 | 2/2019 | Agustsson et al. |
| 10,232,193 | B2 | 3/2019 | Iseki |
| 10,258,810 | B2 | 4/2019 | Zwart et al. |
| 10,272,264 | B2 | 4/2019 | Ollila et al. |
| 10,279,196 | B2 | 5/2019 | West et al. |
| 10,293,184 | B2 | 5/2019 | Pishdad et al. |
| 10,307,614 | B2 | 6/2019 | Schnarr |
| 10,307,615 | B2 | 6/2019 | Ollila et al. |
| 10,315,047 | B2 | 6/2019 | Glimelius et al. |
| 10,413,755 | B1 | 9/2019 | Sahadevan |
| 10,449,389 | B2 | 10/2019 | Ollila et al. |
| 10,485,988 | B2 | 11/2019 | Kuusela et al. |
| 10,525,285 | B1 | 1/2020 | Friedman |
| 10,549,117 | B2 | 2/2020 | Vanderstraten et al. |
| 10,549,177 | B2 | 2/2020 | Scheper et al. |
| 10,603,514 | B2 | 3/2020 | Grittani et al. |
| 10,609,806 | B2 | 3/2020 | Roecken et al. |
| 10,636,609 | B1 | 4/2020 | Bertsche et al. |
| 10,660,588 | B2 | 5/2020 | Boyd et al. |
| 10,661,100 | B2 | 5/2020 | Shen |
| 10,682,528 | B2 | 6/2020 | Ansorge et al. |
| 10,702,716 | B2 | 7/2020 | Heese |
| 10,758,746 | B2 | 9/2020 | Kwak et al. |
| 10,870,018 | B2 | 12/2020 | Bartkoski et al. |
| 10,918,886 | B2 | 2/2021 | Smith et al. |
| 11,554,271 | B2* | 1/2023 | Smith ................ A61N 5/1081 |
| 2007/0287878 | A1 | 12/2007 | Fantini et al. |

(56) References Cited

U.S. PATENT DOCUMENTS

| | | |
|---|---|---|
| 2008/0023644 A1 | 1/2008 | Pedroni |
| 2009/0052623 A1 | 2/2009 | Tome et al. |
| 2009/0063110 A1 | 3/2009 | Failla et al. |
| 2009/0084984 A1 | 4/2009 | Hernandez |
| 2009/0287467 A1 | 11/2009 | Sparks et al. |
| 2010/0119032 A1 | 5/2010 | Yan et al. |
| 2010/0177870 A1 | 7/2010 | Nord et al. |
| 2010/0178245 A1 | 7/2010 | Arnsdorf et al. |
| 2010/0260317 A1 | 10/2010 | Chang et al. |
| 2011/0006224 A1 | 1/2011 | Maltz et al. |
| 2011/0091015 A1 | 4/2011 | Yu et al. |
| 2011/0135058 A1 | 6/2011 | Sgouros et al. |
| 2012/0006271 A1 | 1/2012 | Van Dine et al. |
| 2012/0076271 A1 | 3/2012 | Yan et al. |
| 2012/0157746 A1 | 6/2012 | Meltsner et al. |
| 2012/0171745 A1 | 7/2012 | Itoh |
| 2012/0197058 A1 | 8/2012 | Shukla et al. |
| 2013/0116929 A1 | 5/2013 | Carlton et al. |
| 2013/0150922 A1 | 6/2013 | Butson et al. |
| 2013/0177641 A1 | 7/2013 | Ghoroghchian |
| 2013/0231516 A1 | 9/2013 | Loo et al. |
| 2014/0020692 A1 | 1/2014 | Kawata et al. |
| 2014/0177807 A1 | 6/2014 | Lewellen et al. |
| 2014/0185776 A1 | 7/2014 | Li et al. |
| 2014/0206926 A1 | 7/2014 | van der Laarse |
| 2014/0275706 A1 | 9/2014 | Dean et al. |
| 2014/0369476 A1 | 12/2014 | Harding |
| 2015/0011817 A1 | 1/2015 | Feng |
| 2015/0202464 A1 | 7/2015 | Brand et al. |
| 2015/0306423 A1 | 10/2015 | Bharat et al. |
| 2016/0279444 A1 | 9/2016 | Schlosser |
| 2016/0310764 A1 | 10/2016 | Bharadwaj et al. |
| 2016/0331997 A1 | 11/2016 | Vilsmeier |
| 2017/0021194 A1 | 1/2017 | Nelms |
| 2017/0028220 A1 | 2/2017 | Schulte et al. |
| 2017/0080253 A1* | 3/2017 | Clayton ............ A61N 5/1067 |
| 2017/0173366 A1 | 6/2017 | Froehlich et al. |
| 2017/0189721 A1 | 7/2017 | Sumanaweera et al. |
| 2017/0203129 A1 | 7/2017 | Dessy |
| 2017/0281973 A1 | 10/2017 | Allen et al. |
| 2018/0021594 A1 | 1/2018 | Papp et al. |
| 2018/0043183 A1 | 2/2018 | Sheng et al. |
| 2018/0056090 A1 | 3/2018 | Jordan et al. |
| 2018/0099154 A1 | 4/2018 | Prieels |
| 2018/0099155 A1 | 4/2018 | Prieels et al. |
| 2018/0099159 A1 | 4/2018 | Forton et al. |
| 2018/0154183 A1 | 6/2018 | Sahadevan |
| 2018/0197303 A1 | 7/2018 | Jordan et al. |
| 2018/0200540 A1* | 7/2018 | Flynn ............ A61N 5/1001 |
| 2018/0207425 A1 | 7/2018 | Carlton et al. |
| 2018/0236268 A1 | 8/2018 | Zwart et al. |
| 2018/0369611 A1 | 12/2018 | Owens et al. |
| 2019/0022407 A1 | 1/2019 | Abel et al. |
| 2019/0022422 A1 | 1/2019 | Trail et al. |
| 2019/0054315 A1 | 2/2019 | Isola et al. |
| 2019/0070435 A1 | 3/2019 | Joe Anto et al. |
| 2019/0168027 A1 | 6/2019 | Smith et al. |
| 2019/0255361 A1 | 8/2019 | Mansfield |
| 2019/0299027 A1 | 10/2019 | Fujii et al. |
| 2019/0299029 A1 | 10/2019 | Inoue |
| 2019/0335125 A1 | 10/2019 | Ito et al. |
| 2019/0336793 A1 | 11/2019 | Zhou et al. |
| 2019/0351259 A1 | 11/2019 | Lee et al. |
| 2020/0001118 A1 | 1/2020 | Snider, III et al. |
| 2020/0002248 A1 | 1/2020 | Krupa et al. |
| 2020/0022248 A1 | 1/2020 | Yi et al. |
| 2020/0030633 A1 | 1/2020 | Van Heteren et al. |
| 2020/0035438 A1 | 1/2020 | Star-Lack et al. |
| 2020/0069818 A1 | 3/2020 | Jaskula-Ranga et al. |
| 2020/0164224 A1 | 5/2020 | Vanderstraten et al. |
| 2020/0178890 A1 | 6/2020 | Otto |
| 2020/0197730 A1 | 6/2020 | Safavi-Naeini et al. |
| 2020/0254279 A1 | 8/2020 | Ohishi |
| 2020/0269068 A1 | 8/2020 | Abel et al. |
| 2020/0276456 A1 | 9/2020 | Swerdloff |
| 2020/0282234 A1 | 9/2020 | Folkerts et al. |
| 2020/0286601 A1* | 9/2020 | Khuntia ............ G16H 15/00 |

FOREIGN PATENT DOCUMENTS

| | | |
|---|---|---|
| CN | 107362464 A | 11/2017 |
| CN | 109966662 A | 7/2019 |
| CN | 111481840 A | 8/2020 |
| CN | 111481841 A | 8/2020 |
| EA | 010207 | 6/2008 |
| EP | 0979656 A2 | 2/2000 |
| EP | 2617283 A1 | 7/2013 |
| EP | 3338858 A1 | 6/2018 |
| EP | 3384961 A1 | 10/2018 |
| EP | 3421087 A1 | 1/2019 |
| EP | 3453427 A1 | 3/2019 |
| EP | 3463427 | 4/2019 |
| EP | 3586920 A1 | 1/2020 |
| JP | 2617283 B2 | 6/1997 |
| JP | 2019097969 A | 6/2019 |
| WO | 2005035061 A2 | 4/2005 |
| WO | WO-2007017177 A1 | 2/2007 |
| WO | WO-2010018476 A2 | 2/2010 |
| WO | WO-2013081218 A2 | 6/2013 |
| WO | WO-2013133936 A1 | 9/2013 |
| WO | WO-2014139493 A1 | 9/2014 |
| WO | WO-2015038832 A1 | 3/2015 |
| WO | 2015054314 A1 | 4/2015 |
| WO | WO-2015102680 A2 | 7/2015 |
| WO | WO-2016122957 A1 | 8/2016 |
| WO | WO-2017156316 A1 | 9/2017 |
| WO | WO-2017174643 A1 | 10/2017 |
| WO | WO-2018137772 A1 | 8/2018 |
| WO | WO-2018152302 A1 | 8/2018 |
| WO | 2019016301 | 1/2019 |
| WO | 2019016305 | 1/2019 |
| WO | 2019018813 A1 | 1/2019 |
| WO | WO-2019097250 A1 | 5/2019 |
| WO | WO-2019103983 A1 | 5/2019 |
| WO | WO-2019164835 A1 | 8/2019 |
| WO | WO-2019166702 A1 | 9/2019 |
| WO | WO-2019185378 A1 | 10/2019 |
| WO | WO-2019222436 A2 | 11/2019 |
| WO | WO-2020018904 A1 | 1/2020 |
| WO | WO-2020064832 A1 | 4/2020 |
| WO | WO-2020107121 A1 | 6/2020 |
| WO | WO-2020159360 A1 | 8/2020 |

OTHER PUBLICATIONS

Brahim Oraiqat et al., "An Ionizing Radiation Acoustic Imaging (iRAI) Technique for Real-Time Dosimetric Measurements for FLASH Radiotherapy," Medical Physics, vol. 47, Issue10, Oct. 2020, pp. 5090-5510first published: Jun. 27, 2020, rattps://doi.org/10.1002/mp.14358.

K. Petersson et al., "Dosimetry of ultra high dose rate irradiation for studies on the biological effect induced in normal brain and GBM," ICTR-PHE 2016, p. S84, Feb. 2016,; rattps://publisher-connector.core.ac.uk/resourcesync/data/elsevier/pdf/14c/1:1HR0cDovL2FwaS51bHNIdmllci5jb20vY29udGVudC9hcnRpY2xIL3BpaS9zMDE2NzgxNDAxNjMwMTcyNA==.pdf.

Susanne Auer et al., "Survival of tumor cells after proton irradiation with ultra-high dose rates," Radiation Oncology 011, 6:139, Published Oct. 18, 2011,; POI: https://doi.org/10.1186/1748-717X-6-139.

Cynthia E. Keen, "Clinical linear accelerator delivers FLASH radiotherapy," Physics World, Apr. 23, 2019, IOP Publishing Ltd,; rattps://physicsworld.com/a/clinical-linear-accelerator-delivers-flash-radiotherapy/.

Fan et al., "Emission guided radiation therapy for lung and prostate cancers: A feasibility study on a digital patient," Med Phys. Nov. 2012; 39(11): 7140-7152. Published online Nov. 5, 2012. https://www.ncbi.nlm.nih_gov/pmc/articles/PMC3505203/; oi: 10.1118/1.4761951.

(56) References Cited

OTHER PUBLICATIONS

Favaudon et al., "Ultrahigh dose-rate, "flash" irradiation minimizes the side-effects of radiotherapy," Cancer / Radiotherapy, vol. 19, Issues 6-7 , Oct. 2015 , pp. 526-531, Available online Aug. 12, 2015, https://doi.org/10.1016/j.canrad.2015.04.006.

D. Zlobinskaya et al., "The Effects of Ultra-High Dose Rate Proton Irradiation on Growth Delay in the Treatment of Human Tumor Xenografts in Nude Mice," Radiation Research, 181(2):177-183. Published Feb. 13, 2014,; POI: http://dx.doi.org/10.1667/RR13464.1.

Bjorn Zackrisson, "Biological Effects Of High Energy Radiation And Ultra High Dose Rates," UMEA University Medical Dissertations, New series No. 315—ISSN 0346-6612, From the Department of Oncology, University of Umea, Umea, Sweden, ISBN 91-7174-614-5, Printed in Sweden by the Printing Office of Umea University, Umea, 1991.

P. Montay-Gruel et al., "Irradiation in a flash: Unique sparing of memory in mice after whole brain irradiation with dose rates above 100 Gy/s," Radiotherapy and Oncology, vol. 124, Issue 3, Sep. 2017, pp. 365-369,; available online May 22, 2017,; oi:10.1016/j.radonc.2017.05.003.

BW Loo et al., "Delivery of Ultra-Rapid Flash Radiation Therapy and Demonstration of Normal Tissue Sparing After Abdominal Irradiation of Mice," International Journal of Radiation Oncology, Biology, Physics,; vol. 98, Issue 2, p. E16, Supplement: S Meeting Abstract: P003, Published: Jun. 1, 2017, POI: https://doi.org/10.1016/j.ijrobp.2017.02.101.

Bhanu Prasad Venkatesulu et al., "Ultra high dose rate (35 Gy/sec) radiation does not spare the normal tissue n cardiac and splenic models of lymphopenia and gastrointestinal syndrome," Sci Rep 9, 17180 (2019), Published; O Nov. 2019,; DOI: https://doi.org/10.1038/s41598-019-53562-y.

P. Montav-Gruel et al., "Long-term neurocognitive benefits of FLASH radiotherapy driven by reduced reactive oxygen species," PNAS May 28, 2019, vol. 116, No. 22, pp. 10943-10951; first published May 16, 2019, https://doi.org/10.1073/pnas.1901777116.

Peter G. Maxim et al., "FLASH radiotherapy: Newsflash or flash in the pan?", Medical Physics, 46 {10), October eo19, pp. 4287-4290, American Association of Physicists in Medicine, First published: Jun. 27, 2019, https://doi.org/10.1002/mp_ 13685.

Andrei Pugachev et al., "Pseudo beam's-eye-view as applied to beam orientation selection in intensity-modulated adiation therapy," Int. J. Radiation Oncology Biol. Phys., vol. 51, Issue 5, P1361-1370, Dec. 1, 2001, POI: https://doi.org/10.1016/S0360-3016(01)01736-9.

Xiaodong Zhang et al., "Intensity-Modulated Proton Therapy Reduces the Dose to Normal Tissue Compared With; Intensity-Modulated Radiation Therapy or Passive Scattering Proton Therapy and Enables Individualized Radical Radiotherapy for Extensive Stage IIIB Non-Small-Cell Lung Cancer: A Virtual Clinical Study," Int. J_ Radiation Oncology Biol. Phys., vol. 77, No. 2, pp. 357-366, 2010, Available online Aug. 5, 2009,; DOI: httos://doi.ora/10.1016/i.iirobo.2009.04.028.

A. J. Lomax et al., "Intensity modulated proton therapy: A clinical example," Medical Physics, vol. 28, Issue 3, Mar. 2001, pp. 317-324, First published: Mar. 9, 2001,; https://doi.org/10.1118/1.1350587.

Amberto Widesott et al., "Intensity-Modulated Proton Therapy Versus Helical Tomotherapy in Nasopharynx Cancer: Planning Comparison and NTCP Evaluation," Int. J. Radiation Oncology Biol. Phys., vol. 72, No. 2, pp. 589-p. 96, Oct. 1, 2008, Available online Sep. 13, 2008,; POI: https://doi.org/10.1016/j.ijrobp.2008.05.065.

Andrei Pugachev et al., "Role of beam orientation optimization in intensity-modulated radiation therapy," Int. J. Radiation Oncology Biol. Phys., vol. 50, No. 2, pp. 551-560, Jun. 1, 2001, Available online May 10, 2001,; POI: https://doi.org/10.1016/S0360-3016(01)01502-4.

Damien C. Weber et al., "Radiation therapy planning with photons and protons for early and advanced breast cancer: an overview," Radial Oneal. 2006; 1: 22. Published online Jul. 20, 2006,; oi: 10.1186/1748-717X-1-22.

RaySearch Laboratories, "Leading the way in cancer treatment, Annual Report 2013," RaySearch Laboratories (publ), Stockholm, Sweden, 94 pages, Apr. 2014,; https://www.raysearchlabs.com/siteassets/about-overview/media-center/wp-re-ev-n-pdfs/brochures/raysearch-ar-2013 ng.pdf.

Fredrik Carlsson, "Utilizing Problem Structure in Optimization of Radiation Therapy," KTH Engineering Sciences, Doctoral Thesis, Stockholm, Sweden, Apr. 2008, Optimization and Systems Theory, Department of Mathematics, Royal Institute of Technology, Stockholm, Sweden, ISSN 1401-2294, https://www.raysearchlabs.com/globalassets/about-overview/media-center/wp-re-ev-n-pdfs/publications/thesis-fredrik_light.pdf.

Chang-Ming Charlie Ma, "Physics and Dosimetric Principles of SRS and SBRT," Mathews J Cancer Sci. 4(2): 22, 019, published: Dec. 11, 2019, ISSN: 2474-6797, DOI: https://doi.org/10.30654/MJCS.10022.

Alterego-admin, "Conventional Radiation Therapy May Not Protect Healthy Brain Cells,"; International Neuropsychiatric Association—INA, Oct. 10, 2019, https://inawebsite.org/conventional-radiation-therapy-may-not-protect-healthy-brain-cells/.

Vladimir Anferov, "Scan pattern optimization for uniform proton beam scanning," Medical Physics, vol. 36, Issue 8, Aug. 2009, pp. 3560-3567, First published: Jul. 2, 2009.

Ryosuke Kohno et al., "Development of Continuous Line Scanning System Prototype for Proton Beam Therapy," International Journal of Particle Therapy, Jul. 11, 2017, vol. 3, Issue 4, p. 429-438,; bOI: 10.14338/IJPT-16-00017.1.

Inenbo Gu et al., "Integrated Beam Orientation and Scanning-Spot Optimization in Intensity Modulated Proton Therapy for Brain and Unilateral Head and Neck Tumors," Med Phys. Author manuscript; available in PMC Apr. 1, 2019 https://www.ncbi.nlm.nih.gov/pmc/articles/PMC5904040/; Published in final edited form as: Med Phys_ Apr. 2018; 45(4): 1338-1350. Published online Mar. 1, 2018 .; oi: 10.1002/mp_ 12788 Accepted manuscriptonline: Feb. 2, 2018.

Paul Morel et al., "Spot weight adaptation for moving target in spot scanning proton therapy," Frontiers in Oncology, May 28, 2015, vol. 5, Article 119, 7 pages, doi: 10.3389/fonc.2015.00119.

Simeon Nill et al., "Inverse planning of intensity modulated proton therapy," Zeitschrift fur Medizinische Physik, vol. 14, Issue 1, 2004, pp. 35-40, https://doi.org/1O.1078/0939-3889-00198.

A. Lomax, "Intensity modulation methods for proton radiotherapy," Physics in Medicine & Biology, Jan. 1999, vol. J4, No. 1, pp. 185-205, doi: 10.1088/0031-9155/44/1/014.

M Kramer et al., "Treatment planning for heavy-ion radiotherapy: physical beam model and dose optimization," Physics in Medicine & Biology, 2000, vol. 45, No. 11, pp. 3299-3317, doi: 10.1088/0031-9155/45/11/313.

Harald Paganetti, "Proton Beam Therapy," Jan. 2017, Physics World Discovery, IOP Publishing Ltd, Bristol, UK, 34 pages, DOI: 10.1088/978-0-7503-1370-4.

Shinichi Shimizu et al., "A Proton Beam Therapy System Dedicated lo Spot-Scanning Increases Accuracy with Moving Tumors by Real-Time Imaging and Gating and Reduces Equipment Size," PLoS One, Apr. 18, 2014, Volume; . Issue 4, e94971, https://doi.org/10.1371/journal.pone.0094971.

Heng Li et al., "Reducing Dose Uncertainty for Spot-Scanning Proton Beam Therapy of Moving Tumors by Optimizing he Spot Delivery Sequence," International Journal of Radiation Oncology, Biology, Physics, vol. 93, Issue 3, Nov. 1, 2015, pp. 547-556, available online Jun. 18, 2015, htlps://doi.org/10.1016/j.ijrobp.2015.06.019.

Ion Beam Applications SA, "Netherlands Proton Therapy Center Delivers First Clinical Flash Irradiation," Imaging Technology News, May 2, 2019, Wainscot Media,; https://www.itnonline.com/content/netherlands-proton-therapy-center-delivers-first-clinical-flash-irradiation.

(56) References Cited

OTHER PUBLICATIONS

Aafke Christine Kraan, "Range verification methods in particle therapy: underlying physics and Monte Carlo modeling," Frontiers in Oncology, Jul. 7, 2015, vol. 5, Article 150, 27 pages, doi: 10.3389/fonc.2015.00150.

Wayne D. Newhauser et al., "The physics of proton therapy," Physics in Medicine & Biology, Mar. 24, 2015, 60 R155-R209, Institute of Physics and Engineering in Medicine, IOP Publishing, doi: 10. 1088/0031-9155/60/8/R155.

Se McGowan et al., "Treatment planning optimisation in proton therapy," Br J Radiol, 2013, 86, 20120288, The British Institute of Radiology, 12 pages, DOI: 10_1259_bjr_20120288.

Steven Van De Water et al., "Towards FLASH proton therapy: the impact of treatment planning and machine characteristics on achievable dose rates," Acta Oncologica, Jun. 26, 2019, vol. 58, No. 10, p. 1462-1469, Tayloi; !I. Francis Group, DOI: 10_1080/0284186X. 2019_1627416.

J-Groen, "Flash optimisation in clinical IMPT treatment planning," MSc Thesis, Jul. 1, 2020, Erasmus University Medical Center, department of radiotherapy, Delft University of Technology, 72 pages.

Muhammad Ramish Ashraf et al., "Dosimetry for FLASH Radiotherapy: A Review of Tools and the Role of Radioluminescence and Cherenkov Emission," Frontiers in Oncology, Aug. 21, 2020, vol. 8, Article 328, 20 pages, doi: 10.3389/fphy.2020.00328.

Emil Schuler et al., "Experimental Platform for Ultra-high Dose Rate FLASH Irradiation of Small Animals Using a Clinical Linear Accelerator," International Journal of Radiation Oncology, Biology, Physics, vol. 97, No. 1, Sep. 2016, pp. 195-203.

Elette Engels et al., "Toward personalized synchrotron microbeam radiation therapy," Scientific Reports, 10:8833, Jun. 1, 2020, 13 pages, DOI: https://doLorg/10_1038/s41598-020-65729-z.

D-H Mackeprang et al., "Assessing dose rate distributions in VMAT plans" (Accepted Version), Accepted Version: https://boris_unibe. ch/92814/8/dose_rate_project_revised_submitpdf; Published Version: 2016, Physics in medicine and biology, 61(8), pp. 3208-3221 _ Institute of Physics Publishing IOP,; published Mar. 29, 2016, https://boris.unibe_ch/92814/.

Xiaoying Liang et al., "Using Robust Optimization for Skin Flashing in Intensity Modulated Radiation Therapy for Breast Cancer Treatment: A Feasibility Study," Practical Radiation Oncology, vol. 10, Issue 1, p. 59-69, Published DY Elsevier Inc., Oct. 15, 2019.

Alexei Trofimov et al., "Optimization of Beam Parameters and Treatment Planning for Intensity Modulated Proton Therapy," Technology in Cancer Research & Treatment, vol. 2, No. 5, Oct. 2003, p. 437-444, Adenine Press.

R. M. De Kruijff, "Flash radiotherapy: ultra-high dose rates to spare healthy tissue," International Journal of Radiation Biology, 2020, vol. 96, No. 4, pp. 419-423, published online: Dec. 19, 2019, rattps://doi.org/10.1080/09553002.2020.1704912.

Mevion Medical Systems, "Focus On The Future: Flash Therapy," Press Releases, Sep. 16, 2019, https://www.mevion.com/newsroom/press-releases/focus-future-flash-therapy.

Joseph D. Wilson et al., "Ultra-High Dose Rate (FLASH) Radiotherapy: Silver Bullet or Fool's Gold?", Frontiers in Oncology, Jan. 17, 2020, vol. 9, Article 1563, 12 pages, doi: 10.3389/fonc.2019. 01563.

David P. Gierga, "Is Flash Radiotherapy coming?", International Organization for Medical Physics, 2020, rattps://www.iomp.org/iomp-news2-flash-radiotherapy/.

Abdullah Muhammad Zakaria et al., "Ultra-High Dose-Rate, Pulsed (FLASH) Radiotherapy with Carbon Ions: Generation of Early, Transient, Highly Oxygenated Conditions in the Tumor Environment," Radiation Research, Dec. 1, 2020, vol. 194, Issue 6, pp. 587-593, Radiation Research Society, Published: Aug. 27, 2020, oi: https://doi.org/10.1667/RADE-19-00015.1.

Yusuke Demizu et al., "Carbon Ion Therapy for Early-Stage Non-Small-Cell Lung Cancer," BioMed Research International, vol. 2014, Article ID 727962, 9 pages, Hindawi Publishing Corporation, published: Sep. 11, 2014, rattps://doi.org/10.1155/2014/727962.

Ivana Dokic et al., "Next generation multi-scale biophysical characterization of high precision cancer particle radiotherapy using clinical proton, helium-, carbon- and oxygen ion beams," Oncotarget, Aug. 30, 2016, vol. 7, No. 35, pp. 56676-56689, published online: Aug. 1, 2016,; oi: 10.18632/oncotarget.10996.

Aetna Inc., "Proton Beam, Neutron Beam, and Carbon Ion Radiotherapy," 2020, No. 0270, rattp://www_aetna.com/cpb/medical/data/200_299/0270.html.

Nicholas W. Colangelo et al., "The Importance and Clinical Implications of FLASH Ultra-High Dose-Rate Studies; or Proton and Heavy Ion Radiotherapy," Radial Res. Author manuscript; available in PMC Jan. 1, 2021. rattps://www.ncbi.nlm.nih.gov/pmc/articles/PMC6949397/; Published in final edited form as: Radial Res. Jan. 2020; 193(1): 1-4.; Published online Oct. 28, 2019. doi: 10.1667/RR15537.1.

Vincent Favaudon et al., "Ultrahigh dose-rate FLASH irradiation increases the differential response between hormal and tumor tissue in mice," Science Translational Medicine, Jul. 16, 2014, vol. 6, Issue 245, 245ra93, American Association for the Advancement of Science,; DOI: 10.1126/scitranslmed.3008973.

FlashRad: Ultra-high dose-rate FLASH radiotherapy to minimize the complications of radiotherapy, 2014, rattps://siric.curie.fr/sites/default/files/atoms/filesfflashrad.pdf.

Tami Freeman, "Flash radiotherapy: from preclinical promise to the first human treatment," Physics World, 06 Aug 019, IOP Publishing Ltd,; rattps://physicsworld.com/afflash-radiotherapy-from-preclinical-promise-to-the-first-human-treatment/.

Intraop Medical, Inc., "IntraOp and Lausanne University Hospital Announce Collaboration in FLASH radiotherapy," Jun. 18, 2020,; rattps://intraop.com/news-events/lausanne-university-flash-radiotherapy-collaboration/.

M. C. Vozenin et al., "Biological Benefits of Ultra-high Dose Rate FLASH Radiotherapy: Sleeping Beauty Awoken,"; Clin Oneal (R Coll Radial). Author manuscript; available in PMC Nov. 12, 2019. rattps://www.ncbi.nlm.nih.gov/pmc/articles/PMC6850216/; Published in final edited form as: Clin Oneal (R Coll Radial). Jul. 2019; 31(7): 407-415.; Published online Apr. 19, 2019. doi: 10.1016/j_clon.2019.04.001.

Efstathios Kamperis et al., "A Flash back to radiotherapy's past and then fast forward to the future," J Cancer Prev Curr Res. 2019;10(6):142-144. published Nov. 13, 2019,; POI: 10.15406/jcpcr.2019.10.00407.

P. Symonds et al., "FLASH Radiotherapy: The Next Technological Advance in Radiation Therapy?", Clinical Oncology, vol. 31, Issue 7, p. 405-406, Jul. 1, 2019, The Royal College of Radiologists, Published by Elsevier Ltd., POI: https://doi.org/10.1016/j.clon.2019. 05.011.

Swati Girdhani et al., "Abstract LB-280: Flash: A novel paradigm changing tumor irradiation platform that; enhances therapeutic ratio by reducing normal tissue toxicity and activating immune pathways," Proceedings: MCR Annual Meeting 2019; Mar. 29-Apr. 3, 2019; Atlanta, GA, published Jul. 2019, vol. 79, Issue 13 Supplement, pp. B-280, American Association for Cancer Research,; DOI: httos://doi.om/10.1158/1538-7445.AM2019-LB-280.

Bazalova-Carter et al., "On the capabilities of conventional x-ray tubes to deliver ultra-high (FLASH) dose rates," Med. Phys. Dec. 2019; 46 (12):5690-5695, published Oct. 23, 2019, American Association of Physicists in Medicine; oi: 10.1002/mp.13858. Epub Oct. 23, 2019. PMID: 31600830.

Manuela Buonanno et al., "Biological effects in normal cells exposed to FLASH dose rate protons," Radiother; Oncol. Author manuscript; available in PMC Oct. 1, 2020. https://www.ncbi.nlm.nih.gov/pmc/articles/PMC6728238/; Published in final edited form as: Radiother Oneal. Oct. 2019; 139: 51-55.; Published online Mar. 5, 2019. doi: 10.1016/i.radonc.2019.02.009.

N. Rama et al., "Improved Tumor Control Through T-cell Infiltration Modulated by Ultra-High Dose Rate Proton FLASH Using a Clinical Pencil Beam Scanning Proton System," International Journal of Radiation Oncology, Biology, Physics, vol. 105, Issue 1, Supplement, S164-S165, Sep. 1, 2019, Mini Oral Sessions, DOI: https://doi.org/10.1016/j.ijrobp.2019.06.187.

Inserm Press Office, "Radiotherapy 'flashes' to reduce side effects," Press Release, Jul. 16, 2014, https://presse.inserm.fr/en/radiotherapy-flashes-to-reduce-side-effects/13394/.

(56) References Cited

OTHER PUBLICATIONS

Eric S. Diffenderfer et al., "Design, Implementation, and in Vivo Validation of a Novel Proton FLASH Radiation Therapy System," International Journal of Radiation Oncology, Biology, Physics, vol. 106, Issue 2, 1 February 020, pp. 440-448, Available online Jan. 9, 2020, Published by Elsevier Inc., POI: https://doi.org/10.1016/j.ijrobp.2019.10.049.

Valerie Devillaine, "Radiotherapy and Radiation Biology," Institut Curie, Apr. 21, 2017, https:1/institut-curie_org/page/radiotherapy-and-radiation-biology.

Imaging Technology News, "ProNova and medPhoton to Offer Next Generation Beam Delivery, Advanced Imaging for Proton Therapy," Oct. 6, 2014, Wainscot Media,; Link: https://www.itnonline.com/contenl/pronova-and-medphoton--offer-next-generation-beam-delivery-advanced- Imaging-proton-therapy.

Oncolink Team, "Radiation Therapy: Which type is right for me?", Oncolink Penn Medicine, last reviewed 3 March 020, Trustees of the University of Pennsylvania,; https://www_oncolink.org/cancer-treatmenl/radiation/introduction-to-radiation-therapy/radiation-therapy-which-type-is-; right-for-me.

Marco Durante et al., "Faster and safer? FLASH ultra-high dose rate in radiotherapy," Br J Radiol 2018; 91(1082): 0170628, British Institute of Radiology, Published Online: Dec. 15, 2017,; rattps://doi.org/10.1259/bjr-20170628.

John R. Fischer, "PMB launches FLASH radiotherapy system for use in clinical trials," HealthCare Business News, Jun. 9, 2020, DOTmed_com, Inc_,; rattps://www_dotmed.com/news/story/51662.

Marie-Catherine Vozenin et al., "The advantage of FLASH radio-therapy confirmed in mini-pig and cat-cancer patients," Clinical Cancer Research, Author Manuscript Published OnlineFirst Jun. 6, 2018, https://clincancerres.aacrjournals_org/contenl/clincanres/early/2018/06/06/1078-0432_CCR-17-3375Jull _pdf.

M. McManus et al., "The challenge of ionisation chamber dosimetry in ultra-short pulsed high dose-rate Very High Energy Electron beams," Sci Rep 10, 9089 (2020), published Jun. 3, 2020, https://doi.org/10.1038/s41598-020-65819-y.

Ibrahim Oraiqat et al., "An Ionizing Radiation Acoustic Imaging (iRAI) Technique for Real-Time Dosimetric Measurements for FLASH Radiotherapy," Medical Physics, vol. 47, IssueIO, Oct. 2020, pp. 5090-51 Ofirst published: Jun. 27, 2020, rattps://doi.org/10.1002/mp.14358.

K. Petersson et al., "Dosimetry of ultra high dose rate irradiation for studies on the biological effect induced in normal brain and GBM," ICTR-PHE 2016, p. S84, Feb. 2016,; https://publisher-connector.core.ac.uk/resourcesync/data/elsevier/pdf/14c/; 1:1HR0cDovL2FwaS51bHNIdmllci5jb20vY29udGVudC9hcnRpY2xIL3BpaS9zMDE2Nzg xNDAxNiMwMTcyNA==. pdf.

Favaudon et al., "Ultrahigh dose-rate, "flash" irradiation minimizes the side-effects of radiotherapy," Cancer / Radiotherapy, vol. 19, Issues 6-7, Oct. 2015, pp. 526-531, Available online Aug. 12, 2015, https://doi.Org/10.1016/i.canrad.2015.04.006.

O. Zlobinskaya et al., "The Effects of Ultra-High Dose Rate Proton Irradiation on Growth Delay in the Treatment of Human Tumor Xenografts in Nude Mice," Radiation Research, 181 (2):177-183. Published Feb. 13, 2014,; POI: http://dx.doi.Org/10.1667/RR13464.1.

P. Montay-Gruel et al., "Irradiation in a flash: Unique sparing of memory in mice after whole brain irradiation with dose rates above 100 Gy/s," Radiotherapy and Oncology, vol. 124, Issue 3, Sep. 2017, pp. 365-369,; available online May 22, 2017,; oi: 10.1016/i.radonc.2017.05.003.

Lamberto Widesott et al., "Intensity-Modulated Proton Therapy Versus Helical Tomotherapy in Nasopharynx Cancer: Planning Comparison and NTCP Evaluation," Int. J. Radiation Oncology Biol. Phys., vol. 72, No. 2, pp. 589-p. 96, Oct. 1, 2008, Available online Sep. 13, 2008,; POI: https://doi.Org/10.1016/i.iirobp.2008.05.065.

Alterego-Admin, "Conventional Radiation Therapy May Not Protect Healthy Brain Cells," International Neuropsychiatric Association—INA, Oct. 10, 2019, https://inawebsite.org/conventional-radiation-therapy-may-not-protect-healthy-brain-cells/.

Steven Van De Water et al., "Towards FLASH proton therapy: the impact of treatment planning and machine characteristics on achievable dose rates," Acta Oncologica, Jun. 26, 2019, vol. 58, No. 10, p. 1462-1469, Tayloi; II. Francis Group, DOI: 101080/0284186X.2019 1627416.

P.H Mackeprang et al., "Assessing dose rate distributions in VMAT plans" (Accepted Version), Accepted Version:; https://boris_unibe.ch/92814/8/dose_rate_project_revised_submitpdf; Published Version: 2016, Physics in medicine and biology, 61 (8), pp. 3208-3221 _ Institute of Physics Publishing IOP,; published Mar. 29, 2016, https://boris.unibe ch/92814/;.

Wenbo Gu et al., "Integrated Beam Orientation and Scanning-Spot Optimization in Intensity Modulated Proton Therapy for Brain and Unilateral Head and Neck Tumors," Med Phys. Author manuscript; available in PMC Apr. 1, 2019 https://www.ncbi.nlm.nih.gov/pmc/articles/PMC5904040/; Published in final edited form as: Med Phys_ Apr. 2018; 45(4): 1338-1350. Published online Mar. 1, 2018.; oi: 10.1002/mp_ 12788 Accepted manuscriptonline: Feb. 2, 2018.

Simeon Nill et al., "Inverse planning of intensity modulated proton therapy," Zeitschrift fur Medizinische Physik, vol. 14, Issue 1, 2004, pp. 35-40, https://doi.org/10.1078/0939-3889-00198.

Heng Li et al., "Reducing Dose Uncertainty for Spot-Scanning Proton Beam Therapy of Moving Tumors by Optimizing he Spot Delivery Sequence," International Journal of Radiation Oncology, Biology, Physics, vol. 93, Issue 3, Nov. 1, 2015, pp. 547-556, available online Jun. 18, 2015, htlps://doi.org/10.1016/i.ijrobp.2015.06.019.

Yusuke Demizu et al., "Carbon Ion Therapy for Early-Stage Non-Small-Cell Lung Cancer," BioMed Research International, vol. 2014, Article ID 727962, 9 pages, Hindawi Publishing Corporation, published: Sep. 11, 2014, rattps://doi.org/10.1155/2014/727962.

Efstathios Kamperis et al., "A Flash back to radiotherapy's past and then fast forward to the future," J Cancer Prev Curr Res. 2019;10(6): 142-144. published Nov. 13, 2019,; POI: 10.15406/icpcr.2019.10.00407;.

P. Symonds et al., "FLASH Radiotherapy: The Next Technological Advance in Radiation Therapy?", Clinical Oncology, vol. 31, Issue 7, p. 405-406, Jul. 1, 2019, The Royal College of Radiologists, Published by Elsevier Ltd., POI: https://doi.Org/10.1016/i.clon.2019.05.011 .

N. Rama et al., "Improved Tumor Control Through T-cell Infiltration Modulated by Ultra-High Dose Rate Proton FLASH Using a Clinical Pencil Beam Scanning Proton System," International Journal of Radiation Oncology, Biology, Physics, vol. 105, Issue 1, Supplement, S164-S165, Sep. 1, 2019, Mini Oral Sessions, DOI: https://doi.Org/10.1016/i.ijrobp.2019.06.187.

Eric S. Diefenderfer et al., "Design, Implementation, and in Vivo Validation of a Novel Proton FLASH Radiation Therapy System," International Journal of Radiation Oncology, Biology, Physics, vol. 106, Issue 2,1 February 020, pp. 440-448, Available online Jan. 9, 2020, Published by Elsevier Inc., POI: https://doi.Org/10.1016/i.ijrobp.2019.10.049.

Machine Translation of Guoliang, Jiang. "Modern oncology radiotherapy", published Jun. 30, 2003 by Shanghai Science and Technology Publishing House.

* cited by examiner

FLASH THERAPY TREATMENT PLANNING AND ONCOLOGY INFORMATION SYSTEM HAVING DOSE RATE PRESCRIPTION AND DOSE RATE MAPPING

CROSS-REFERENCE TO RELATED APPLICATION

This is a continuation application of co-pending U.S. patent application Ser. No. 18/087,398 entitled "Flash Therapy Treatment Planning and Oncology Information System having Dose Rate Prescription and Dose Rate Mapping," by Christel Smith et al., filed Dec. 22, 2022, which is a continuation application of U.S. patent application Ser. No. 17/147,353 entitled "Flash Therapy Treatment Planning and Oncology Information System having Dose Rate Prescription and Dose Rate Mapping," by Christel Smith et al., filed Jan. 12, 2021, which is a continuation application of U.S. patent application Ser. No. 16/436,762 entitled "Flash Therapy Treatment Planning and Oncology Information System having Dose Rate Prescription and Dose Rate Mapping," by Christel Smith et al., filed Jun. 10, 2019, the entire contents of all of which are incorporated herein by reference.

FIELD OF THE INVENTION

Embodiments of the present invention are generally related to integrated circuit structures used in memory systems that can be used by computer systems, including embedded computer systems.

BACKGROUND OF THE INVENTION

The use of radiation therapy to treat cancer is well known. Typically, radiation therapy involves directing a beam of high energy proton, photon, ion, or electron radiation ("therapeutic radiation") into a target or target volume (e.g., a tumor or lesion).

Before a patient is treated with radiation, a treatment plan specific to that patient is developed. The plan defines various aspects of the therapy using simulations and optimizations based on past experiences. In general, the purpose of the treatment plan is to deliver sufficient radiation to the target while minimizing exposure of surrounding normal, healthy tissue to the radiation.

The planner's goal is to find a solution that is optimal with respect to multiple clinical goals that may be contradictory in the sense that an improvement toward one goal may have a detrimental effect on reaching another goal. For example, a treatment plan that spares the liver from receiving a dose of radiation may result in the stomach receiving too much radiation. These types of tradeoffs lead to an iterative process in which the planner creates different plans to find the one plan that is best suited to achieving the desired outcome.

A recent radiobiology study has demonstrated the effectiveness of delivering an entire, relatively high therapeutic radiation dose to a target within a single, short period of time, in one fraction or possible a handful of fractions. This type of treatment is referred to generally herein as FLASH radiation therapy (FLASH RT). Evidence to date suggests that FLASH RT advantageously spares normal, healthy tissue from damage when that tissue is exposed to only a single irradiation for only a very short period of time. FLASH RT thus introduces important constraints that are not considered in or achieved with conventional radiation treatment planning.

Ultra-high dose rate radiotherapy or FLASH therapy delivers high doses of radiation at very high-speed achieving dose rates of 40 Gy/s and above. Pre-clinical studies have shown that delivering radiotherapy at such ultra-high dose rates allows comparable tumor control while sparing the healthy tissue thereby reducing toxicities. The mechanism of action behind this so-called FLASH effect is still under investigation but it is becoming increasingly clear that the time a tissue is irradiated, the dose applied and therefore the dose rate are critical parameters that play a role in the FLASH effect.

Current treatment planning systems (TPS) are restricted to prescribing dose and displaying dose as a distribution overlaid on a patient's CT scan. Since dose rate and such FLASH relevant parameters are now of importance, being able to prescribe dose rate of a certain threshold to a certain specific tissue structure (healthy tissue, organs at risk, margin, and clinical tumor volume) will be crucial for treating humans with Flash. Furthermore, this input of prescription will provide clinicians and researchers valuable information that can further be correlated with biological parameters and patient outcome.

SUMMARY OF THE INVENTION

Embodiments of the present invention implement a computing system comprising a central processing unit (CPU), and memory coupled to the CPU and having stored therein instructions that, when executed by the computing system, cause the computing system to execute operations to generate a radiation treatment plan. The operations include accessing a minimum prescribed dose to be delivered into and across the target, determining a number of beams and directions of the beams, wherein the directions are determined such that the beams do not overlap outside the target, and determining a beam energy for each of the beams, wherein the number of beams, the directions of the beams, and the beam energy for each of the beams are determined such that the entire target receives the minimum prescribed dose. The operations further include prescribing a dose rate, dose rate definition, and optimizing dose rate constraints for a FLASH therapy, while displaying a dose rate map of the FLASH therapy.

In one embodiment, a physician is provided access to a drop down menu that will allow a selection of a desired dose rate definition. In one embodiment, the desired dose rate definition includes an average field dose rate, a local dose rate, a spot dose rate, an instantaneous dose rate, or a dose rate threshold.

In one embodiment, the physician can select the dose rate value after the dose rate definition is selected. In one embodiment, the physician can apply a dose rate prescription to a plurality of fields, structures, sub-structures, or groupings of voxels.

In one embodiment, the dose rate prescription is passed through a quality assurance step, where the dose rate prescription is verified before patient treatment. In one embodiment, a record and verify system records a dose and a dose rate during the time of delivery.

In one embodiment, the present invention is implemented as a non-transitory computer-readable storage medium having computer-executable instructions for causing a computing system to perform a method of generating a radiation treatment plan. The method includes accessing values of parameters from memory of the computing system, wherein the parameters comprise directions of beams to be directed into sub-volumes in a target and beam energies for the beams, accessing information that specifies limits for the radiation treatment plan, wherein the limits comprise a maximum limit on irradiation time for each sub-volume outside the target, and adjusting the values of the parameters until the irradiation time for said each sub-volume outside the target satisfies the maximum limit on irradiation time. The method further includes prescribing a dose rate and optimizing dose rate constraints for a FLASH therapy, and displaying a dose rate map of the FLASH therapy.

The foregoing is a summary and thus contains, by necessity, simplifications, generalizations and omissions of detail; consequently, those skilled in the art will appreciate that the summary is illustrative only and is not intended to be in any way limiting. Other aspects, inventive features, and advantages of the present invention, as defined solely by the claims, will become apparent in the non-limiting detailed description set forth below.

BRIEF DESCRIPTION OF THE DRAWINGS

The present invention is illustrated by way of example, and not by way of limitation, in the figures of the accompanying drawings and in which like reference numerals refer to similar elements.

DETAILED DESCRIPTION

Figure 1:
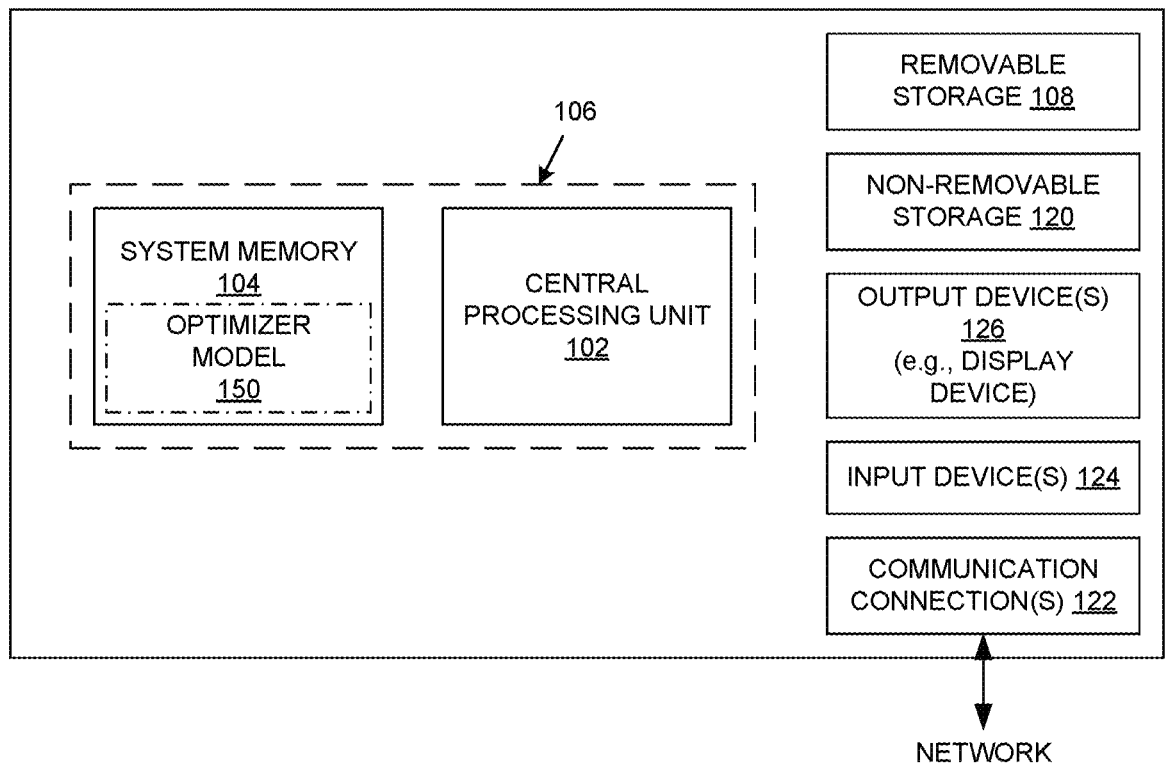
FIG. 1 is a block diagram of an example of a computing system upon which the embodiments described herein may be implemented.

Reference will now be made in detail to the various embodiments of the present disclosure, examples of which are illustrated in the accompanying drawings. While described in conjunction with these embodiments, it will be understood that they are not intended to limit the disclosure to these embodiments. On the contrary, the disclosure is intended to cover alternatives, modifications and equivalents, which may be included within the spirit and scope of the disclosure as defined by the appended claims. Furthermore, in the following detailed description of the present disclosure, numerous specific details are set forth in order to provide a thorough understanding of the present disclosure. However, it will be understood that the present disclosure may be practiced without these specific details. In other instances, well-known methods, procedures, components, and circuits have not been described in detail so as not to unnecessarily obscure aspects of the present disclosure.

Some portions of the detailed descriptions that follow are presented in terms of procedures, logic blocks, processing, and other symbolic representations of operations on data bits within a computer memory. These descriptions and representations are the means used by those skilled in the data processing arts to most effectively convey the substance of their work to others skilled in the art. In the present application, a procedure, logic block, process, or the like, is conceived to be a self-consistent sequence of steps or instructions leading to a desired result. The steps are those utilizing physical manipulations of physical quantities. Usually, although not necessarily, these quantities take the form of electrical or magnetic signals capable of being stored, transferred, combined, compared, and otherwise manipulated in a computing system. It has proven convenient at times, principally for reasons of common usage, to refer to these signals as transactions, bits, values, elements, symbols, characters, samples, pixels, or the like.

It should be borne in mind, however, that all of these and similar terms are to be associated with the appropriate physical quantities and are merely convenient labels applied to these quantities. Unless specifically stated otherwise as apparent from the following discussions, it is appreciated that throughout the present disclosure, discussions utilizing terms such as "determining," "accessing," "directing," "controlling," "defining," "arranging," "generating," "representing," "applying," "adding," "multiplying," "adjusting," "calculating," "predicting," "weighting," "assigning," "using," "identifying," "reducing," "downloading," "reading," "computing," "storing," or the like, refer to actions and processes of a computing system or similar electronic computing device or processor (e.g., the computing system 100 of FIG. 1). The computing system or similar electronic computing device manipulates and transforms data represented as physical (electronic) quantities within the computing system memories, registers or other such information storage, transmission or display devices. Terms such as "dose" or "fluence" generally refer to a dose or fluence value; the use of such terms will be clear from the context of the surrounding discussion.

Portions of the detailed description that follows are presented and discussed in terms of a method. Although steps and sequencing thereof are disclosed in figures herein describing the operations of this method, such steps and sequencing are exemplary. Embodiments are well suited to performing various other steps or variations of the steps recited in the flowchart of the figure herein, and in a sequence other than that depicted and described herein.

Embodiments described herein may be discussed in the general context of computer-executable instructions residing on some form of computer-readable storage medium, such as program modules, executed by one or more computers or other devices. By way of example, and not limitation, computer-readable storage media may comprise non-transitory computer storage media and communication media. Generally, program modules include routines, programs, objects, components, data structures, etc., that perform particular tasks or implement particular abstract data types. The functionality of the program modules may be combined or distributed as desired in various embodiments.

Computer storage media includes volatile and nonvolatile, removable and non-removable media implemented in any method or technology for storage of information such as computer-readable instructions, data structures, program modules or other data. Computer storage media includes, but is not limited to, random access memory (RAM), read only memory (ROM), electrically erasable programmable ROM (EEPROM), flash memory or other memory technology, compact disk ROM (CD-ROM), digital versatile disks (DVDs) or other optical storage, magnetic cassettes, magnetic tape, magnetic disk storage or other magnetic storage devices, or any other medium that can be used to store the desired information and that can accessed to retrieve that information.

Communication media can embody computer-executable instructions, data structures, and program modules, and includes any information delivery media. By way of example, and not limitation, communication media includes wired media such as a wired network or direct-wired connection, and wireless media such as acoustic, radio frequency (RF), infrared and other wireless media. Combinations of any of the above can also be included within the scope of computer-readable media.

FIG. 1 shows a block diagram of an example of a computing system 100 upon which the embodiments described herein may be implemented. In its most basic configuration, the system 100 includes at least one processing unit 102 and memory 104. This most basic configuration is illustrated in FIG. 1 by dashed line 106. The system 100 may also have additional features and/or functionality. For example, the system 100 may also include additional storage (removable and/or non-removable) including, but not limited to, magnetic or optical disks or tape. Such additional storage is illustrated in FIG. 1 by removable storage 108 and non-removable storage 120. The system 100 may also contain communications connection(s) 122 that allow the device to communicate with other devices, e.g., in a networked environment using logical connections to one or more remote computers.

The system 100 also includes input device(s) 124 such as keyboard, mouse, pen, voice input device, touch input device, etc. Output device(s) 126 such as a display device, speakers, printer, etc., are also included.

In the example of FIG. 1, the memory 104 includes computer-readable instructions, data structures, program modules, and the like associated with an "optimizer" model 150. However, the optimizer model 150 may instead reside in any one of the computer storage media used by the system 100, or may be distributed over some combination of the computer storage media, or may be distributed over some combination of networked computers. The functionality of the optimizer model 150 is described below.

Figure 2:
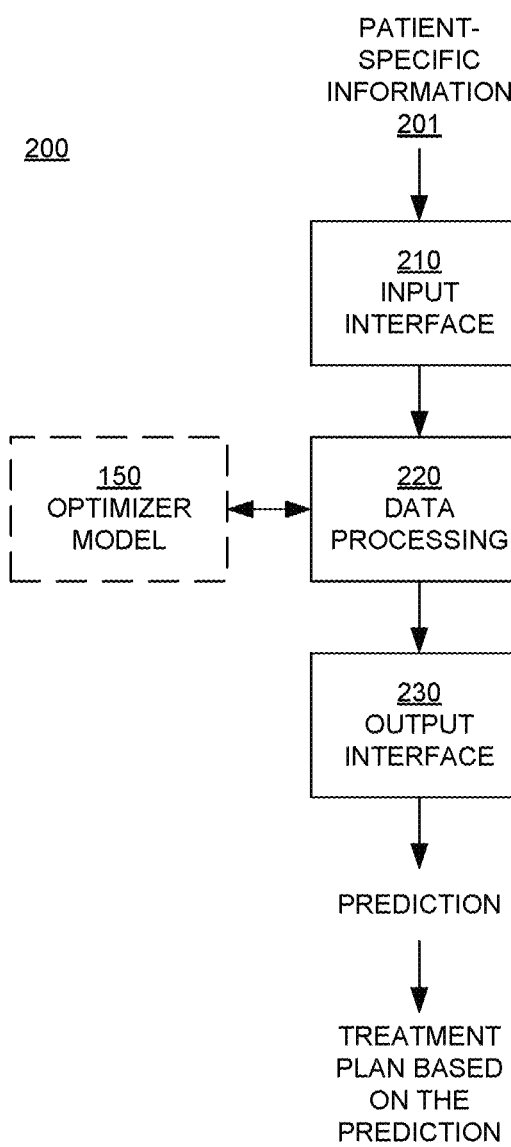
FIG. 2 is a block diagram illustrating an example of an automated radiation therapy treatment planning system in embodiments according to the present invention.

FIG. 2 is a block diagram illustrating an example of an automated radiation therapy treatment planning system 200 in embodiments according to the present invention. The system 200 includes an input interface 210 to receive patient-specific information (data) 201, a data processing component 220 that implements the optimizer model 150, and an output interface 230. The system 200 in whole or in part may be implemented as a software program, hardware logic, or a combination thereof on/using the computing system 100 (FIG. 1).

In the example of FIG. 2, the patient-specific information is provided to and processed by the optimizer model 150. The optimizer model 150 yields a prediction result. A treatment plan based on the prediction result can then be generated.

Figure 3:
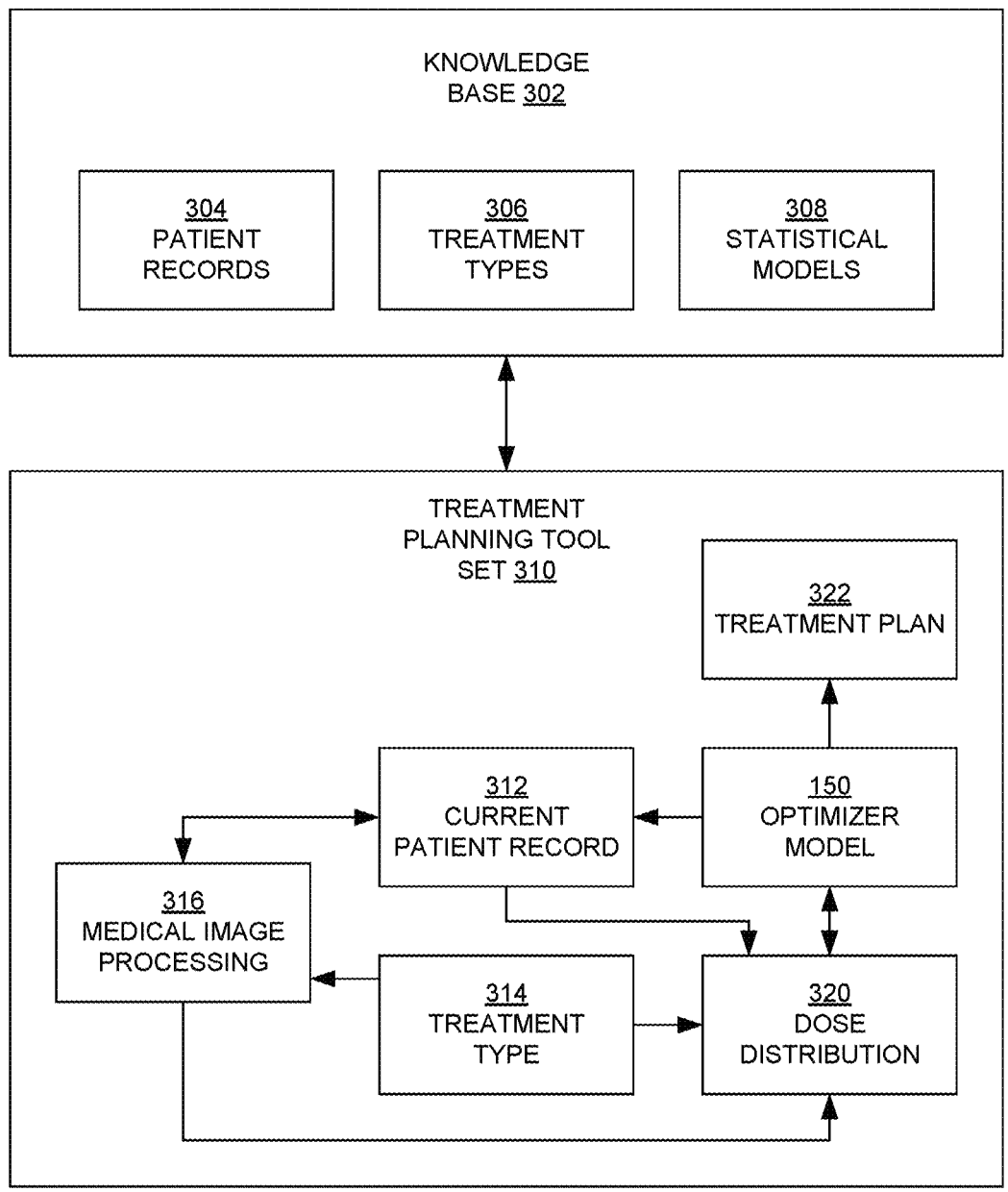
FIG. 3 illustrates a knowledge-based planning system in embodiments according to the present invention.

FIG. 3 illustrates a knowledge-based planning system 300 in embodiments according to the present invention. In the example of FIG. 3, the system 300 includes a knowledge base 302 and a treatment planning tool set 310. The knowledge base 302 includes patient records 304 (e.g., radiation treatment plans), treatment types 306, and statistical models 308. The treatment planning tool set 310 in the example of FIG. 3 includes a current patient record 312, a treatment type 314, a medical image processing module 316, the optimizer model (module) 150, a dose distribution module 320, and a final radiation treatment plan 322.

The treatment planning tool set 310 searches through the knowledge base 302 (through the patient records 304) for prior patient records that are similar to the current patient record 312. The statistical models 308 can be used to compare the predicted results for the current patient record 312 to a statistical patient. Using the current patient record 312, a selected treatment type 306, and selected statistical models 308, the tool set 310 generates a radiation treatment plan 322.

More specifically, based on past clinical experience, when a patient presents with a particular diagnosis, stage, age, weight, sex, co-morbidities, etc., there can be a treatment type that is used most often. By selecting the treatment type that the planner has used in the past for similar patients, a first-step treatment type 314 can be chosen. The medical image processing module 316 provides automatic contouring and automatic segmentation of two-dimensional cross-sectional slides (e.g., from computed tomography or magnetic resonance imaging) to form a three-dimensional (3D) image using the medical images in the current patient record 312. Dose distribution maps are calculated by the dose distribution module 320, which may utilize the optimizer model 150.

In embodiments according to the present invention, the optimizer model 150 uses a dose prediction model to help shape the dose distribution. The optimizer model 150 can provide, for example, a 3D dose distribution, fluences, and associated dose-volume histograms for the current patient.

Figure 4A:
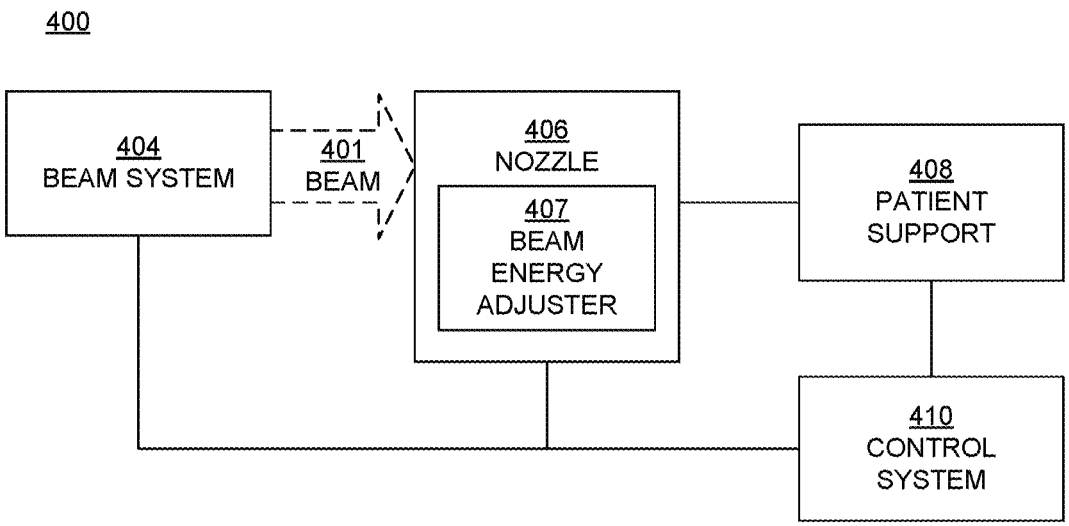
FIG. 4A is a block diagram showing selected components of a radiation therapy system upon which embodiments according to the present invention can be implemented.

FIG. 4A is a block diagram showing selected components of a radiation therapy system 400 upon which embodiments according to the present invention can be implemented. In the example of FIG. 4A, the system 400 includes a beam system 404 and a nozzle 406.

The beam system 404 generates and transports a beam 401 to the nozzle 406. The beam 401 can be a proton beam, electron beam, photon beam, ion beam, or atom nuclei beam (e.g., carbon, helium, and lithium). In embodiments, depending on the type of beam, the beam system 404 includes components that direct (e.g., bend, steer, or guide) the beam system in a direction toward and into the nozzle 406. In embodiments, the radiation therapy system may include one or more multileaf collimators (MLCs); each MLC leaf can be independently moved back-and-forth by the control system 410 to dynamically shape an aperture through which the beam can pass, to block or not block portions of the beam and thereby control beam shape and exposure time. The beam system 404 may also include components that are used to adjust (e.g., reduce) the beam energy entering the nozzle 406.

The nozzle 406 is used to aim the beam toward various locations (a target) within an object (e.g., a patient) supported on the patient support device 408 (e.g., a chair or table) in a treatment room. A target may be an organ, a portion of an organ (e.g., a volume or region within the organ), a tumor, diseased tissue, or a patient outline.

The nozzle 406 may be mounted on or a part of a gantry (FIGS. 4B, 4C, and 4D) that can be moved relative to the patient support device 408, which may also be moveable. In embodiments, the beam system 404 is also mounted on or is a part of the gantry; in another embodiment, the beam system is separate from (but in communication with) the gantry.

The control system 410 of FIG. 4A receives and implements a prescribed treatment plan. In embodiments, the control system 410 includes a computer system having a processor, memory, an input device (e.g., a keyboard), and perhaps a display in well-known fashion. The control system 410 can receive data regarding operation of the system 400. The control system 410 can control parameters of the beam system 404, nozzle 406, and patient support device 408, including parameters such as the energy, intensity, direction, size, and/or shape of the beam, according to data it receives and according to the prescribed treatment plan.

As noted above, the beam entering the nozzle 406 has a specified energy. Thus, in embodiments according to the present disclosure, the nozzle 406 includes one or more components that affect (e.g., decrease, modulate) the energy of the beam. The term "beam energy adjuster" is used herein as a general term for a component or components that affect the energy of the beam, in order to control the range of the beam (e.g., the extent that the beam penetrates into a target), to control the dose delivered by the beam, and/or to control the depth dose curve of the beam, depending on the type of beam. For example, for a proton beam or an ion beam that has a Bragg peak, the beam energy adjuster can control the location of the Bragg peak in the target. In various embodiments, the beam energy adjuster 407 includes a range modulator, a range shifter, or both a range modulator and a range shifter. That is, when the term "beam energy adjuster" is used, then the element being discussed may be a range modulator, a range shifter, or both a range modulator and a range shifter.

Figure 4B:
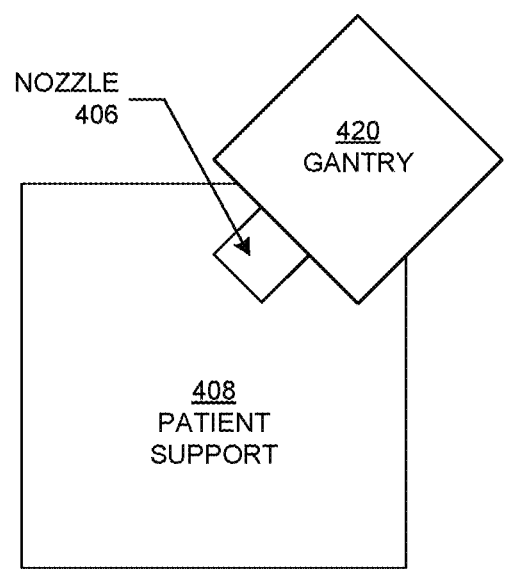
FIG. 4B is a block diagram illustrating a non-coplanar arrangement of a gantry and nozzle relative to a patient support device in embodiments according to the invention.
Figure 4C:
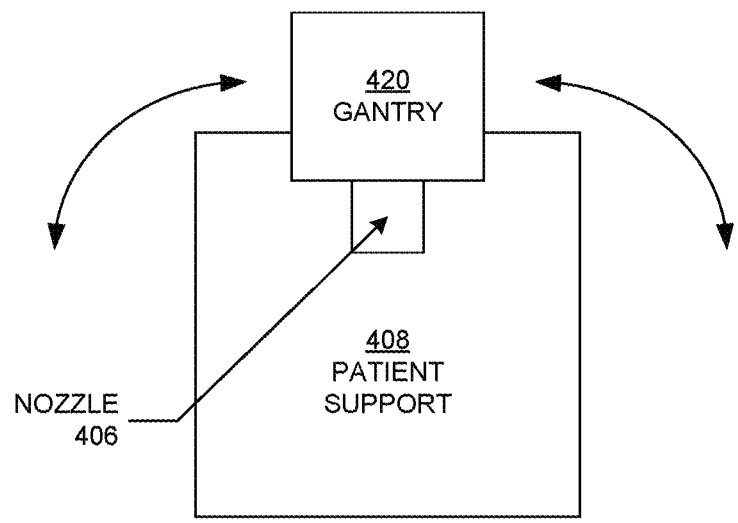
FIG. 4C is a block diagram illustrating a coplanar arrangement of a gantry and nozzle relative to a patient support device in embodiments according to the invention.
Figure 4D:
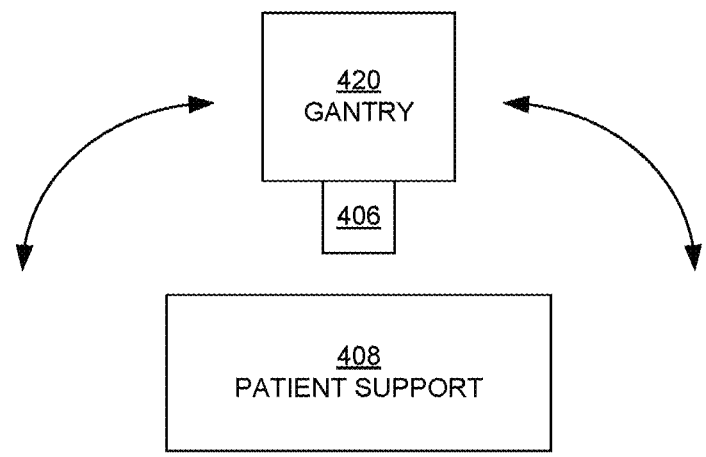
FIG. 4D is a block diagram illustrating movement of a gantry and nozzle around a patient support device in embodiments according to the invention.

FIG. 4B is a block diagram illustrating a non-coplanar arrangement of a gantry 420 and nozzle 406 relative to a patient support device 408 in embodiments according to the invention. FIG. 4C is a block diagram illustrating a coplanar arrangement of a gantry 420 and nozzle 406 relative to a patient support device 408 and also illustrating movement of the gantry and nozzle around the patient support device in embodiments according to the invention. FIG. 4D is a block diagram illustrating movement of the gantry 420 and nozzle 406 around the patient support device 408 in embodiments according to the invention. This movement can occur in either the non-coplanar arrangement or the coplanar arrangement.

Figure 5:
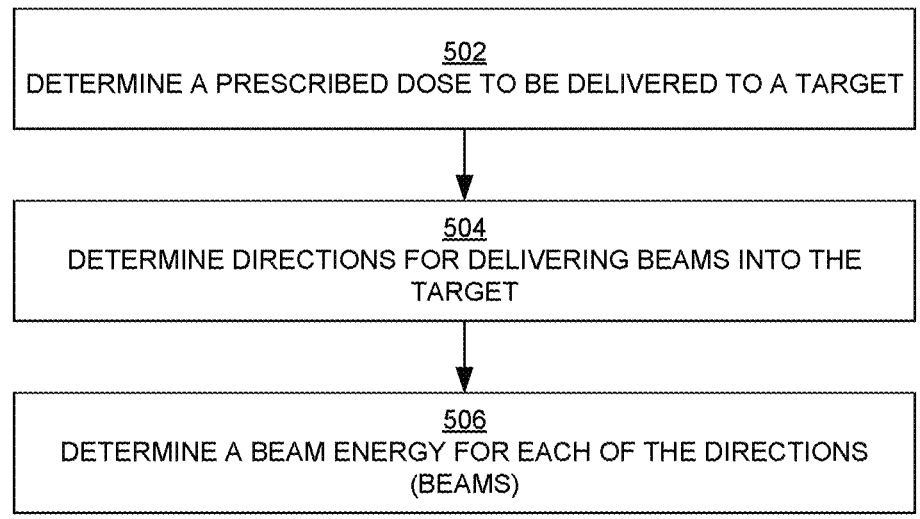
FIG. 5 is a flowchart of an example of computer-implemented operations for generating a radiation treatment plan in embodiments according to the present invention.

FIG. 5 is a flowchart 500 of an example of computer-implemented operations for generating a radiation treatment plan in embodiments according to the present invention. The flowchart 500 can be implemented as computer-executable instructions (e.g., the optimizer model 150 of FIG. 1) residing on some form of computer-readable storage medium (e.g., using the computing system 100 of FIG. 1).

In intensity modulated radiation therapy (IMRT) such as intensity modulated particle therapy (IMPT), beam intensity is varied across each treatment region (target) in a patient. Depending on the treatment modality, the degrees of freedom available for intensity modulation include beam shaping (collimation), beam weighting (spot scanning), and angle of incidence (which may be referred to as beam geometry). These degrees of freedom lead to an effectively infinite number of potential treatment plans, and therefore consistently and efficiently generating and evaluating high-quality treatment plans is beyond the capability of a human and relies on the use of a computing system, particularly considering the time constraints associated with the use of radiation therapy to treat ailments like cancer, as well as the large number of patients that are undergoing or need to undergo radiation therapy during any given time period.

In block 502 of FIG. 5, a prescribed dose to be delivered into and across the target is determined. Each portion of the target can be represented by at least one 3D element known as a voxel; a portion may include more than one voxel. A portion of a target or a voxel may also be referred to herein as a sub-volume; a sub-volume may include one or more portions or one or more voxels. As will be described in detail below, each portion or voxel may receive radiation from one or more beams delivered from different directions. The prescribed dose defines, for example, a dose value, or a minimum dose value and a maximum dose value, for each portion or voxel of the target. In embodiments, the prescribed dose is the same for all portions (sub-volumes or voxels) of the target, such that a uniform dose is prescribed for the entire target.

In block 504, directions (e.g., gantry angles relative to the patient or target, or nozzle directions relative to the patient or target) for delivering beams into the target are determined. The beams can be proton beams, electron beams, photon beams, ion beams, or atom nuclei beams. The operation of determining beam directions can include determining the number of beams (the number of directions from which beams are to be delivered). The beams' paths may or may not overlap within the target, and may or may not overlap outside the target. In general, when generating the radiation treatment plan, one goal is to determine beam paths that minimize the irradiation time of each sub-volume or voxel of the tissue outside the target. Ideally, each sub-volume or voxel outside the target is intersected, at most, by only a single beam. If some overlap between beam paths is permitted, then ideally each sub-volume or voxel outside the target is intersected by not more than two beams, with most intersected by only a single beam. In embodiments, as one means of achieving the aforementioned goal, the beam directions are determined such that the total amount of overlap between the beams' paths is minimized outside the target. In one such embodiment, the directions are determined such that the paths of the beams overlap within the target and such that the total amount of overlap of the beams' paths outside the target is less than the total amount of the overlap of the beams' paths within the target. In another such embodiment, the directions are determined so that the paths of the beams do not overlap at all outside the target. The beams' paths can lie within the same plane, or they can be in different planes. Additional information is provided in conjunction with FIGS. 6A, 6B, 6C, and 6D.

Any number of other factors may be considered when determining the beam directions. These factors may include the shape and size (e.g., height H and width W, or diameter) of the beam in the beam's eye view (see FIG. 7A). These factors may also include, for example, the amount or type of healthy tissue that a beam will be traveling through. That is, one beam direction may be more favorable than another if it travels a shorter distance through healthy tissue or avoids passing through a vital organ and may be weighted accordingly.

In block 506 of FIG. 5, a beam energy or intensity is determined for each of the directions (for each of the beams). The beam energy or intensity for each direction is determined such that the predicted or calculated cumulative doses (e.g., doses calculated using the optimizer model 150 of FIG. 1) at locations inside the target satisfy the prescribed dose as defined in block 502. As noted, beam paths may or may not overlap in the target; if the beams' paths overlap in the target, then the beam energy or intensity for each direction is determined such that the predicted or calculated cumulative doses (e.g., doses calculated using the optimizer model 150 of FIG. 1) at locations inside the target where the beams' paths overlap satisfy the prescribed dose as defined in block 502. In embodiments, a beam includes a number of beam segments or beamlets. In one or more such embodiments, a maximum energy (e.g., 80 MeV) for the beam is specified, and an energy for each of the beam segments is determined as a percentage (100 percent or less) or equivalent fraction of the maximum beam energy. In general, beams can have the same energy or different energies, and each beam can have a range of energies. Thus, different energies or intensities can be delivered in different directions, and different energies or intensities can be delivered in each direction. Additional information is provided in conjunction with FIG. 7A.

While the operations in blocks 502, 504, and 506 of FIG. 5 are presented as occurring in series and in a certain order, the present invention is not so limited. The operations may be performed in a different order and/or in parallel, and they may also be performed in an iterative manner, as the number of beams (and accordingly, the number of directions), the beam directions, and the beam energies or intensities (and/or beam segment energies or intensities) used to deliver the prescribed dose are interrelated. As noted above, because of the different parameters that need to be considered, the range of values for those parameters, the interrelationship of those parameters, the need for treatment plans to be effective yet minimize risk to the patient, and the need to generate high-quality treatment plans quickly, the use of the optimizer model 150 executing consistently on the computing system 100 (FIG. 1) for radiation treatment planning as disclosed herein is important.

The discussion to follow refers to beams, targets, doses, and other elements or values. The discussion below is in the context of modeled elements and calculated values in the treatment planning tool set 310 and the optimizer model 150 (FIG. 3), unless otherwise noted or made clear in the discussion.

Figure 6A:
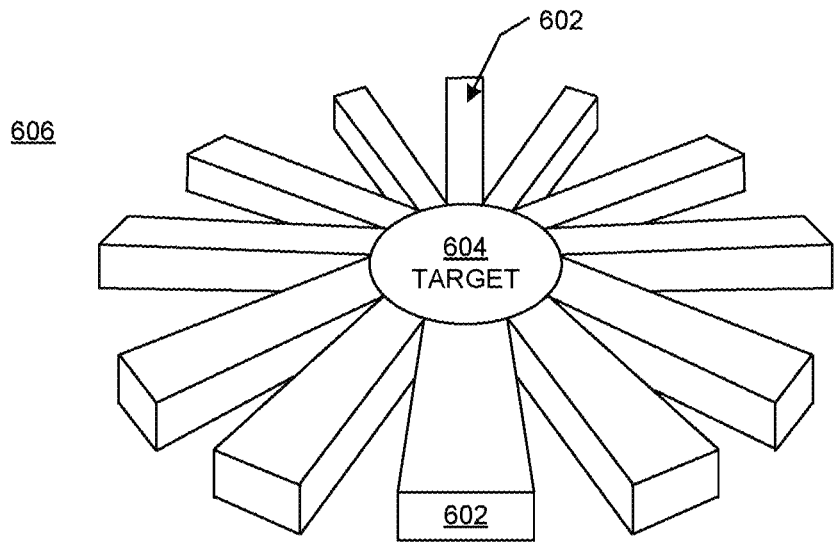
FIG. 6A illustrates a perspective view of an example of a beam geometry in embodiments according to the invention.

FIG. 6A illustrates a perspective view of an example of a beam geometry in embodiments according to the invention. In the example of FIG. 6A, the beams (exemplified by beam 602) are in the same plane. The beams can be proton beams, electron beams, photon beams, ion beams, or atom nuclei beams. Each beam can deliver a relatively high dose in a relatively short period of time. For example, in embodiments, each beam can deliver doses sufficient for FLASH RT (e.g., at least four (4) grays (Gy) in less than one second, and as much as 20 Gy or 50 Gy or more in less than one second). In embodiments, the range is 0.01-500 Gy. As described herein, each beam can include one or more beam segments or beam lets. In this example, the beams' paths overlap only within the target 604, and do not overlap outside the target in the surrounding tissue 606.

In the example of FIG. 6A, the beam 602 (for example) is illustrated as passing completely through the target 604. For beams that have a Bragg peak (e.g., proton beams and ion beams), the ranges of the beams can be controlled so that the beam does not pass completely through the target, as will be described further below.

Although multiple beams are shown in FIG. 6A, this does not mean that all beams are necessarily delivered at the same time or in overlapping time periods, although they can be. The number of beams delivered at any one time depends on the number of gantries or nozzles in the radiation treatment system (e.g., the radiation treatment system 400 of FIG. 4A) and on the treatment plan.

Figure 6B:
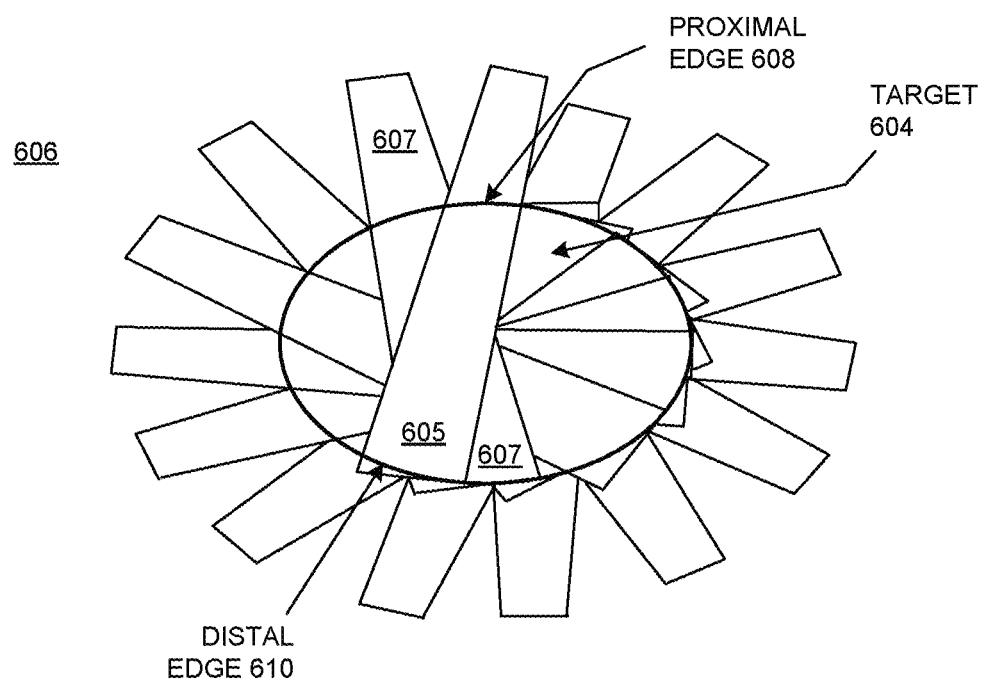
FIG. 6B illustrates a cross-sectional view of an example of a beam geometry in embodiments according to the invention.

FIG. 6B illustrates a cross-sectional view of an example of a beam geometry in embodiments according to the invention. In this example, the beams (exemplified by beams 605 and 606) overlap only within the target and are in the same plane. The figure depicts the beams in overlapping fashion to demonstrate that each portion of the target 604 receives a dose of radiation. The beams can be proton beams, electron beams, photon beams, ion beams, or atom nuclei beams. In the example of FIG. 6B, the beams are illustrated as not extending beyond the distal edge of the target 604 (as would be the case for proton or ion beams, for example); however, the invention is not so limited. Each beam can deliver a relatively high dose in a relatively short period of time. For example, each beam can deliver doses sufficient for FLASH RT.

For implementations in which the beams have a Bragg peak, such as a proton beam or an ion beam, the dose delivered by a beam (or beam segment) is not necessarily uniform along the entire length of the beam path through the target 604. Thus, for example, for a proton or ion beam, the dose delivered by the beam 605 at the proximal portion (or edge) 608 of the target 604 may be different from (e.g., less than) the dose delivered by that beam at the distal portion (or edge) 610 of the target (here, proximal and distal are with reference to the source of the beam 605). The same can be said for each proton or ion beam.

The dose delivered to each portion of the target 604 is cumulative, based on the number of beams that are delivered to and through that portion. For example, the portions of the target 604 covered by the beams 605 and 606 receive a total dose that is the sum of the dose delivered by the beam 605 and the dose delivered by the beam 606. In embodiments, the energies of the beams (beam segments) are accurately determined so that, even though the dose along each beam (or beam segment) is not uniform, a uniform cumulative dose distribution is achieved within and across the target 604.

Figure 6C:
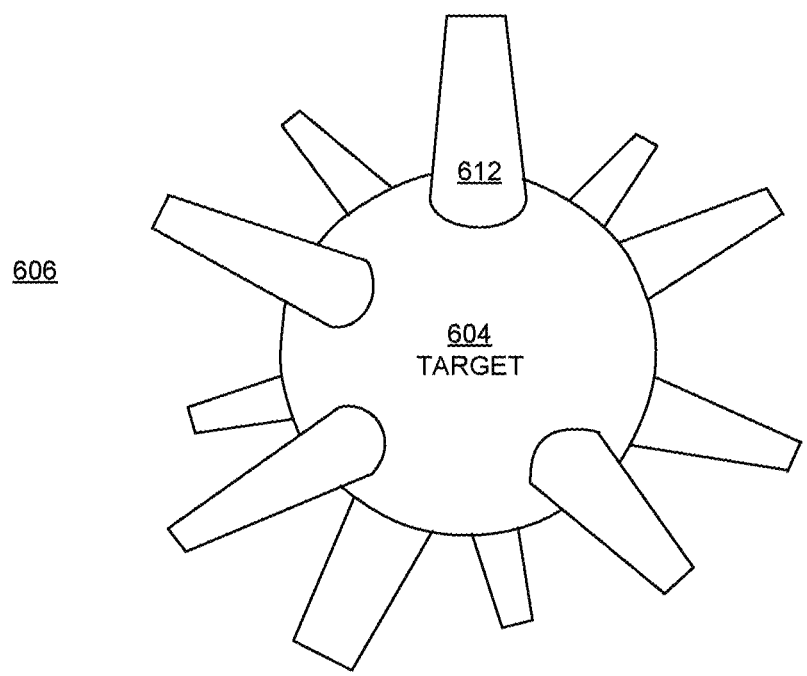
FIG. 6C illustrates a perspective view of an example of a beam geometry in embodiments according to the invention.

FIG. 6C illustrates a perspective view of an example of a beam geometry in embodiments according to the invention. In the example of FIG. 6C, the beams (exemplified by beam 612) are in different planes. As described herein, each beam can include one or more beam segments or beam lets. In this example, the beams' paths overlap only within the target 604, and do not overlap outside the target in the surrounding tissue 606. Although multiple beams are shown in the figure, all beams are not necessarily delivered at the same time or in overlapping time periods as mentioned above. The beams can be proton beams, electron beams, photon beams, ion beams, or atom nuclei beams. Each beam can deliver a relatively high dose in a relatively short period of time. For example, each beam can deliver doses sufficient for FLASH RT.

Figure 6D:
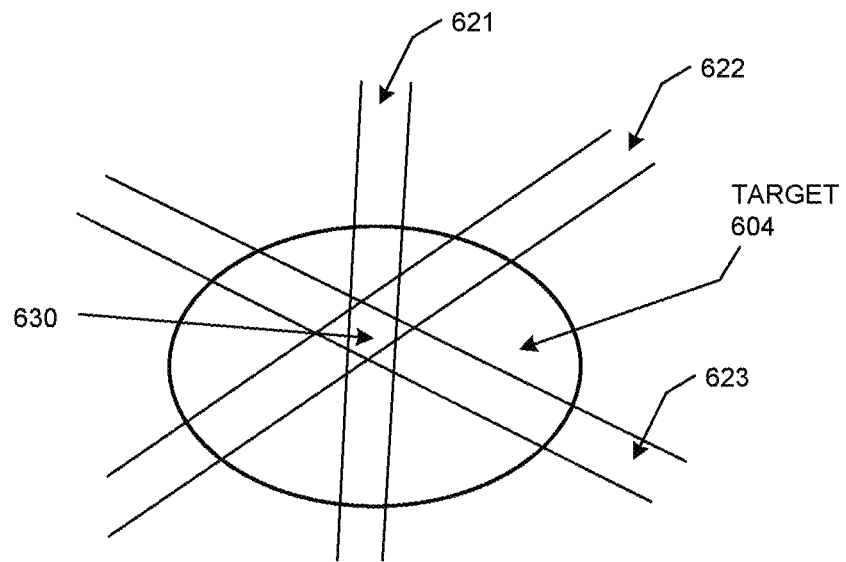
FIG. 6D illustrates a cross-sectional view of an example of a beam geometry in embodiments according to the invention.

FIG. 6D illustrates a cross-sectional view of an example of a beam geometry in embodiments according to the invention. In this example, the beams (exemplified by beams 621, 622, and 623) overlap only within the target and are in the same plane. While three beams are illustrated, the invention is not so limited. As described herein, each beam can include one or more beam segments or beamlets. In this example, the beams' paths overlap only within the target 604, and do not overlap outside the target in the surrounding tissue 606. Although multiple beams are shown in the figure, all beams are not necessarily delivered at the same time or in overlapping time periods as mentioned above. The beams can be proton beams, electron beams, photon beams, ion beams, or atom nuclei beams. Each beam can deliver a relatively high dose in a relatively short period of time. For example, each beam can deliver doses sufficient for FLASH RT.

In the example of FIG. 6D, the beams 621, 622, and 623 intersect at the sub-volume 630, other sub-volumes in the target 604 receive doses from two of the beams, other sub-volumes in the target receive doses from only one of the beams, and yet other sub-volumes do not receive a dose. The directions and/or numbers of beam can be varied over a number of treatment sessions (that is, fractionated in time) so that a uniform dose is delivered across the target.

As mentioned above, for implementations that use proton beams or ion beams, the dose delivered by each beam at the respective proximal portion (or edge) of the target 604 may be different from (e.g., less than) the dose delivered by that beam at the respective distal portion (or edge) of the target (as before, proximal and distal are with reference to the source of the beam).

The dose delivered to each portion of the target 604 is cumulative, based on the number of beams that are delivered to and through that portion. Not all beams are depicted in the figures for simplicity; in general, the number of beams is sufficient to achieve a uniform cumulative dose distribution within the target 604.

In general, the surface of a target can be viewed as having a number of discrete facets. From this perspective, for beams other than photon beams, each incident beam is orthogonal to each facet such that the beams do not overlap outside the target. In the case of photon beams, each incident beam is parallel to the facet and does not overlap other beams outside the target.

Figure 7A:
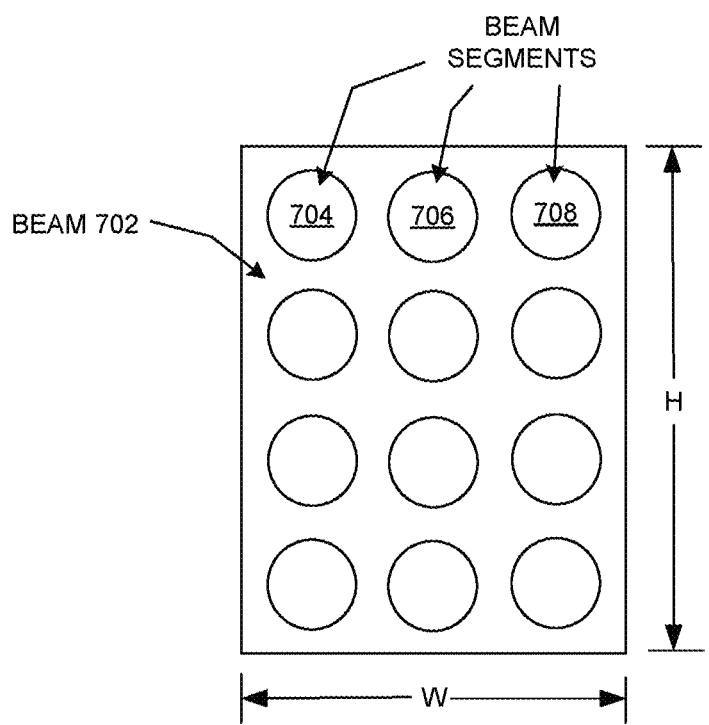
FIG. 7A illustrates a beam's eye view of a beam in embodiments according to the invention.

FIG. 7A illustrates a beam's eye view (BEV) of a beam 702 in embodiments according to the invention. That is, FIG. 7A illustrates a cross-section of a beam. The beams of FIGS. 6A, 6B, 6C, and 6D are examples of the beam 702. The beam 702 is illustrated as being rectangular in shape having a height H and width W. However, the invention is not so limited, and the beam 702 can have virtually any regular or irregular cross-sectional (e.g., BEV) shape. For example, the shape of the beam 702 can be defined using an MLC that blocks a portion or portions of the beam. Different beams can have different shapes.

In the FIG. 7A embodiment, the beam 702 includes a number of beam segments or beam lets (that also may be referred to as spots) exemplified by beam segments 704, 706, and 708. A maximum energy (e.g., 80 MeV) is specified for the beam 702, and an energy level is defined for each of the beam segments as a percentage or fraction of the maximum energy. In essence, each of the beam segments is weighted in terms of its energy level; some beam segments are weighted to have a higher energy level than other beam segments. By weighting the energy per beam segment, in effect the intensity of each beam segment is also weighted. The energy per beam segment is defined so that the beam segment will deliver a fraction of the prescribed dose such that, in combination with the other beam segments in the beam, and in combination with the other beams (and beam segments), a uniform (homogeneous) cumulative dose that satisfies the prescribed dose will be delivered within and across the volume of the target. The defined energy level or intensity can be realized for each beam segment using the beam energy adjuster 407 of FIG. 4A.

Each beam segment can deliver a relatively high dose in a relatively short period of time. For example, each beam segment can deliver at least 4 Gy in less than one second, and may deliver as much as 20 Gy or 50 Gy or more in less than one second. The energy or intensity of each beam segment can be controlled using the beam energy adjuster 407 of FIG. 4A so that the beam segment has sufficient energy to reach the distal edge of the target.

In operation, in embodiments, the beam segments are delivered sequentially. For example, the beam segment 704 is delivered to the target (turned on) and then turned off, then the beam segment 706 is turned on then off, then the beam segment 708 is turned on then off, and so on. Each beam segment may be turned on for only a fraction of a second (on the order of milliseconds).

A FLASH prescription capability in a TPS and OIS (e.g., oncology information system) so that a physician can for example prescribe a certain dose rate based of a selected dose-rate definition (e.g., for example voxel-specific, contour-specific, global beam dose rate, etc.) dose rate threshold or irradiation time for a specific tissue structure. As research in this area progresses, the ability to determine which parameters have the most impact on patient outcome and refine FLASH prescriptions adjusting and optimizing with dose rate parameters becomes important. In addition, dose rate or irradiation times per voxel in 3D or 4D will be displayed similarly to how dose is displayed in the TPS today.

In the prior art, there are currently no dose rate, irradiation time or such parameters included in prescribing a treatment within a TPS or OIS. Making such information available to prescribe dose rate, optimize on dose rate constraints and displaying the dose rate map will allow the clinician to prescribe FLASH therapy in a reliable way while gathering information on the impact of those parameters on patient outcome.

For example, a clinician can decide to prescribe FLASH therapy to a lung cancer patient and determine depending on how dose rate is defined, that they need 90% of the normal lung to be irradiated at FLASH dose rate above 40 Gy/s. As more is learned from pre-clinical studies, perhaps it may be determined brain structures require higher dose rates in order to achieve the FLASH effect, so perhaps for a brain case, the clinician will want to prescribe that normal brain should receive a minimum dose rate of 100 Gy/s. They will also be able to visualize on the dose rate map if the prescription is achieved and make decisions on the course of treatment.

Figure 7B:
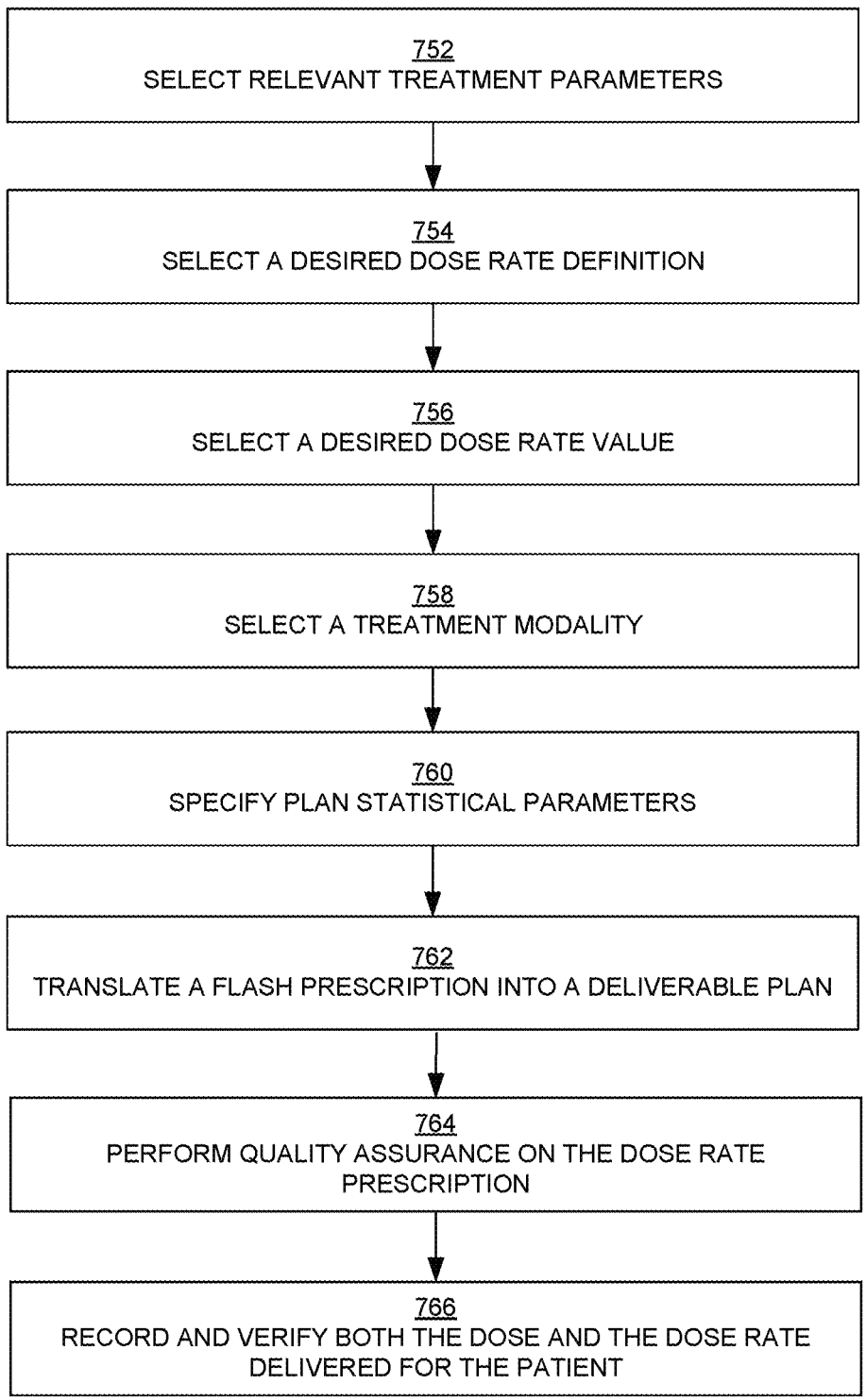
FIG. 7B shows a flowchart of a workflow for prescribing FLASH dose rates in accordance with one embodiment of the present invention.

FIG. 7B shows a flowchart of a workflow for prescribing FLASH dose rates in accordance with one embodiment of the present invention. In one embodiment, the workflow for prescribing dose rate would begin in the physician's intent stage, just prior to treatment planning. At that stage, the physician can select relevant treatment parameters such as the prescription dose and fractionation schedule.

The method 750 begins with step 752, where the physician selects relevant parameters. The physician will have access to a drop down menu that will allow him or her to select the desired dose rate definition. Parameters include, for example, average field dose rate, local dose rate, spot dose rate, instantaneous dose rate, computed with active time or total time, or any other specific definition of biologically relevant dose rate, or time-depended flux pattern, as that information becomes available through pre-clinical research.

In step 754, the physician selects a desired dose rate definition. Once the dose rate definition is selected, the physician can select the dose rate value (40 gy/sec to 120 gy/sec) and above.

In step 756, the physician selects a desired dose rate value. The physician can also select treatment modality (e.g., Bragg-Peak, Transmission, or a hybrid approach).

In step 758, the physician selects a treatment modality. The physician can apply the dose rate prescription to any field, structure, sub-structure, or groupings of voxels.

In step 760, the physician specifies plan statistical parameters. The physician can specify plan statistical parameters such as, for example, 90% of the voxels in healthy lung shall receive dose rate of x and above and no less than 70% of dose delivered at or above 40 Gy/s.

In step 762, a flash prescription is translated into a deliverable plan. In treatment planning the clinician will be able to translate the flash prescription into a deliverable plan. This means optimizing for dose to target simultaneously with optimizing for the dose rate prescription.

In step 764, quality assurance is performed on the dose rate prescription. The dose rate prescription gets passed through to a QA step, where now dose delivered and dose rate delivered is verified before patient treatment.

In step 766, the final step is the OIS acts as the record and verify system during the time of delivery. Recording and verifying both dose and dose-rate delivered for each fraction of the patients treatment. It should be noted that in one embodiment, offline adaptations may occur as well, with dose accumulation and dose-rate tracking. Should the dose or dose-rate deviate from physicians intent, the plan will be sent for re-planning.

The foregoing descriptions of specific embodiments of the present invention have been presented for purposes of illustration and description. They are not intended to be exhaustive or to limit the invention to the precise forms disclosed, and many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the claims appended hereto and their equivalents.

What is claimed is:

1. A radiation therapy system comprising:
a processor; and
memory coupled to the processor, the memory storing instructions that, when executed by the processor, cause the radiation therapy system to
access a prescribed dose to be delivered to a target using a FLASH therapy, and
generate a radiation therapy treatment plan to deliver the prescribed dose using the FLASH therapy, the radiation therapy treatment plan including a beam geometry to deliver the prescribed dose, the beam geometry including a plurality of beams, wherein
a first number of the plurality of beams do not overlap outside the target, and
each of the plurality of beams has a Bragg peak.

2. The radiation therapy system of claim 1, wherein a second number of the plurality of beams overlap within the target.

3. The radiation therapy system of claim 2, wherein a third number of the plurality of beams overlap outside the target, and wherein the third number of the plurality of beams is less than the second number of the plurality of beams.

4. The radiation therapy system of claim 1, wherein a dose delivered by at least a first of the plurality of beams is non-uniform.

5. The radiation therapy system of claim 4, wherein the memory stores instructions that, when executed by the processor, cause the radiation therapy system to determine energies for the plurality of beams such that a uniform cumulative dose distribution is achieved across the target.

6. The radiation therapy system of claim 4, wherein the dose delivered at opposing edges of the target traversed by the first of the plurality of beams is different.

7. The radiation therapy system of claim 1, wherein the memory stores instructions that, when executed by the processor, cause the radiation therapy system to determine directions and beam energies for the plurality of beams.

8. The radiation therapy system of claim 7, wherein the directions and beam energies for the plurality of beams are determined such that the target receives the prescribed dose.

9. The radiation therapy system of claim 1, wherein the plurality of beams are in the same plane.

10. The radiation therapy system of claim 1, wherein the prescribed dose is a minimum prescribed dose.

11. A radiation therapy system comprising:
a processor; and
memory coupled to the processor, the memory storing instructions that, when executed by the processor, cause the radiation therapy system to
access a prescribed dose to be delivered to a target using a FLASH therapy, and
generate a radiation therapy treatment plan to deliver the prescribed dose using the FLASH therapy, the radiation therapy treatment plan including a beam geometry to deliver the prescribed dose, the beam geometry including a plurality of beams, wherein
a dose delivered by at least a first of the plurality of beams is non-uniform, and
each of the plurality of beams has a Bragg peak.

12. The radiation therapy system of claim 11, wherein the memory stores instructions that, when executed by the processor, cause the radiation therapy system to determine energies for the plurality of beams such that a uniform cumulative dose distribution is achieved across the target.

13. The radiation therapy system of claim 11, wherein a dose delivered at opposing edges of the target traversed by the first of the plurality of beams is different.

14. The radiation therapy system of claim 11, wherein a first number of the plurality of beams overlap within the target.

15. The radiation therapy system of claim 11, wherein a first number of the plurality of beams do not overlap outside the target.

16. The radiation therapy system of claim 11, wherein the memory stores instructions that, when executed by the processor, cause the radiation therapy system to determine directions and beam energies for the plurality of beams such that the target receives the prescribed dose.

17. The radiation therapy system of claim 11, wherein the plurality of beams are in the same plane.

* * * * *